United States Patent
Wang et al.

(10) Patent No.: US 11,858,958 B2
(45) Date of Patent: Jan. 2, 2024

(54) BLANK LIPOSOME WITH GINSENOSIDE RG3 OR ITS ANALOG AS MEMBRANE MATERIALS AND PREPARATIONS AND USES THEREOF

(71) Applicant: Shanghai Ginsome Pharmatech Co., Ltd., Shanghai (CN)

(72) Inventors: Jianxin Wang, Shanghai (CN); Chao Hong, Shanghai (CN); Ying Zhu, Shanghai (CN); Jiaxuan Xia, Shanghai (CN); Dan Wang, Shanghai (CN); Yingjiang Chen, Shanghai (CN); Huaxing Zhan, Shanghai (CN)

(73) Assignee: Shanghai Ginsome Pharmatech Co., Ltd., Shanghai (CN)

( * ) Notice: Subject to any disclaimer, the term of this patent is extended or adjusted under 35 U.S.C. 154(b) by 18 days.

(21) Appl. No.: 16/961,899

(22) PCT Filed: Nov. 29, 2019

(86) PCT No.: PCT/CN2019/121880
§ 371 (c)(1),
(2) Date: Jul. 13, 2020

(87) PCT Pub. No.: WO2020/108600
PCT Pub. Date: Jun. 4, 2020

(65) Prior Publication Data
US 2020/0369714 A1  Nov. 26, 2020

(30) Foreign Application Priority Data
Nov. 29, 2018  (CN) .......................... 201811447243.4

(51) Int. Cl.
| | | |
|---|---|---|
| *C07J 17/00* | (2006.01) | |
| *A61P 35/00* | (2006.01) | |
| *A61K 9/127* | (2006.01) | |
| *A61K 47/28* | (2006.01) | |
| *A61K 45/06* | (2006.01) | |
| *C07B 63/04* | (2006.01) | |

(52) U.S. Cl.
CPC .......... *C07J 17/005* (2013.01); *A61K 9/1277* (2013.01); *A61K 47/28* (2013.01); *A61P 35/00* (2018.01); *A61K 45/06* (2013.01); *C07B 63/04* (2013.01)

(58) Field of Classification Search
CPC ...... C07J 17/005; A61K 9/1277; A61K 47/28; A61K 45/06; A61P 35/00; C07B 63/04
See application file for complete search history.

(56) References Cited

FOREIGN PATENT DOCUMENTS

| CN | 103417479 A | 12/2013 |
|---|---|---|
| CN | 106466299 A | 3/2017 |
| CN | 108420793 A | 8/2018 |

OTHER PUBLICATIONS

Yu et al (International Journal of Pharmaceutics 450 (2013) 250-258). (Year: 2013).*

* cited by examiner

*Primary Examiner* — Robert S Cabral
(74) *Attorney, Agent, or Firm* — Weisun Rao; Lili Huang; Venture Partner, LLC

(57) ABSTRACT

The present invention provides a blank liposome with ginsenoside Rg3 or its analog as the membrane material, preparations and uses thereof. The disclosed blank liposome has a membrane comprising a lipid and a ginsenoside analog of Formula I, presenting remarkable advantages in film formation, encapsulation efficiency, targeted drug delivery, blood circulation time, stability, safety and homogeneity. It can also be used to load active substances of drugs and cosmetics, biological agents, polynucleotides or oligonucleotides, and the preparation process is convenient.

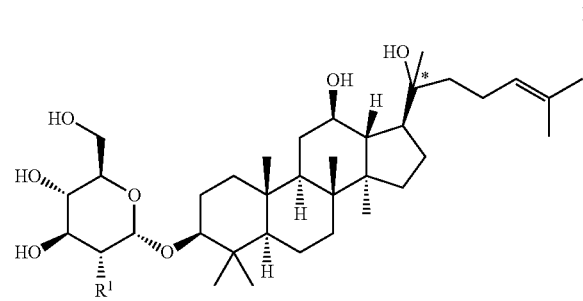

I

28 Claims, 7 Drawing Sheets

BLANK LIPOSOME WITH GINSENOSIDE RG3 OR ITS ANALOG AS MEMBRANE MATERIALS AND PREPARATIONS AND USES THEREOF

CROSS-REFERENCE TO RELATED APPLICATIONS

The application is U.S. national phase under 35 U.S.C. § 371 of international Application No. PCT/CN2019/121880, filed on Nov. 29, 2019, which claims priority to Chinese patent application No. 201811447243.4, filed on Nov. 29, 2018, the contents of which are incorporated herein by reference in their entirety.

The present invention claims the priority of the 2018114472434, filed on Nov. 29, 2018, the contents of which are incorporated herein by its entirety.

FIELD OF INVENTION

The present invention relates to a blank liposome with ginsenoside Rg3 or its analog as membrane materials and preparations and uses thereof.

PRIOR ARTS

Liposomes are lipid bilayer spherical vesicles, which have been used as a novel drug carrier for targeted drug delivery. A drug, whatever in form of powder or solution, can be encapsulated by liposome into a nano-sized lipid bilayer vesicle, having a similar structure to the biological membrane with an internal aqueous phase. Once entering human body, the nanoparticles can be uptaken by reticuloendothelial system (RES) and alter the drug distribution within the body, thereby, enhancing the accumulation of drug in targeted tissue. Thus, it can improve drug efficacy and reduce therapeutic dose, toxicity and side effects.

As asserted in prior arts, Chinese patent application No. CN201210151597.0 discloses a conventional ginsenoside Rg3 liposome and its preparation method. As disclosed, the ginsenoside Rg3 liposome is prepared by dissolving Rg3, phospholipid and cholesterol in an organic solvent, such as n-butanol, ethanol, or sorbitol. Chinese patent application No. CN201610082643.4 discloses a preparation method of 20(R)-Rg3 liposome, where the 20(R)-Rg3 is dissolved in anhydrous ethanol, and then loaded into a blank liposome prepared with phospholipid and cholesterol. Chinese patent application No. CN201611059434.4 discloses a Rh2-ester liposome, preparation method and uses. The Rh2-ester liposome is prepared by dissolving Rh2-ester, lecithin and cholesterol in anhydrous ethanol. Huan Yu, et al disclose a Rg3 liposome and its preparation method, where egg lecithin, ginsenoside Rg3 and cholesterol are dissolved in methanol and then concentrated to form a film. Then the liposome is obtained by film hydration (See: *International Journal of Pharmaceutics* 450(2013): 250-258). As disclosed in this research paper, the mass percentage of Rg3 and lecithin in this Rg3 liposome is in the range of 5-15%. When the percentage is more than 15%, the encapsulation efficiency (EE %) is only 82%.

In the above-mentioned patents and literatures, ginsenoside Rg3 liposome uses lipid and cholesterol as membrane materials, and Rg3 is used as an active substance and encapsulated by the blank liposome.

Chinese patent application No. CN201610693884.2 discloses that ginsenoside with amphiphilic properties, such as ginsenoside Rg5 or Rk1, can be used as membrane materials of liposome. But these ginsenosides must have a lipophilic side and a hydrophilic side, and the lipophilic side must contain at least two double bonds. While Paclitaxel is encapsulated by liposome with ginsenosides such as Rg3 and Rh2 as membrane materials, the obtained Rg3 or Rh2 Paclitaxel liposome are poor in appearance, particle size and stability, and cannot meet the pharmaceutical requirements, especially the particle size and stability. The particle size is more than 1 μm, the encapsulation efficiency is no more than 80% and precipitation appears 7 days after dissolving the liposome in water.

In addition, a long-circulating liposome, capable of biodegradation in vivo, is prepared by surface modification of a conventional liposome in order to achieve the sustained release of drug, maintain a prolonged drug concentration acting on the targeted tissue and enhance the therapeutic efficacy. The surface modifications include polyethylene glycol (PEG) modified phospholipids and nonionic surfactant, such as PEG-DSPC, PEG-PE, PEG-DSPE and PEG-PC etc. Some prior arts disclose long-circulating liposomes, such as, Chinese patent application Nos. CN 201711105675.2, CN 201710993701.3, CN 201611232858.6, CN 201611119508.9 and CN 201610835887.5 etc., but none of them discloses a long-circulating liposome with ginsenoside as membrane material.

Ginsenoside Rg3 and Rh2, only having one double-bond in the lipophilic end, are soluble in methanol and ethanol, poorly soluble in water, insoluble in diethyl ether and chloroform (See: Research progress in ginsenoside Rg3 dosage form, *International Journal of Pharmaceutical Research*, Vol. 44, No. 6, June 2017,).

Therefore, it is necessary to develop a novel liposome with greater drug efficacy, lower hemolysis and better safety. A liposome with ginsenoside Rg3 and Rh2 as membrane material possesses advantages in drug targeting and prolonged circulation, providing a new platform for drug delivery and disease treatment.

CONTENT OF THE PRESENT INVENTION

The present invention provides a novel liposome with gingenoside Rg3 or its analogues as membrane materials, preparations and uses thereof. The novel blank liposome presents advantages in film formation, encapsulation efficiency, drug targeting, blood circulation time, formulation stability, safety and homogeneity, and the preparation process is convenient. The blank liposome in the present invention can encapsulate active substance of drugs and cosmetics, pharmaceutical products, polynucleotide or oligonucleotide to form an active substance-loaded liposome. When the encapsulated substance possesses anti-cancer properties, the loaded liposome shows advantages in targeted drug delivery, anti-multi-drug resistance (MDR), prolonged circulation, less toxicity and drug synergism.

The present invention overcomes the above-mentioned problems through the following techniques.

The present invention provides a blank liposome with a membrane, wherein the membrane comprises a lipid and a ginsenoside analog of Formula I:

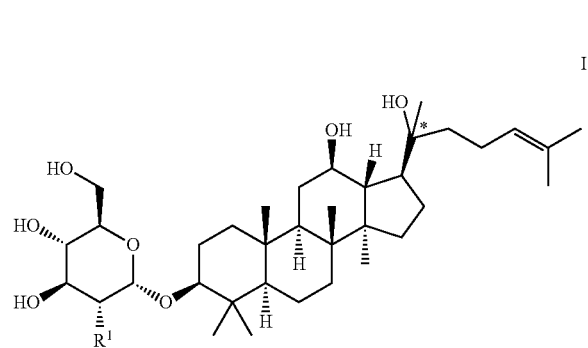

I wherein, "*" represents a chiral carbon; $R^1$ is H, $R^{10}$, $R^{11}$ or hydroxy;

$R^{10}$ is selected from the group consisting of: —O-Glc, —O-Rha, —O-Lyx, —O-Xyl, —O-Ara(p), —O-Ara(f), —O-Glc(2→1)Glc-O-Glc(6→1)Glc, —O-Glc(2→1)Rha, —O-Glc(2→1)Xyl, —O-Glc(6→1)Xyl, —O-Glc(6→1)Rha, —O-Glc(2→1)Ara(p), —O-Glc(6→1)Ara(p), —O-Glc(2→1)Ara(f), —O-Glc(6→1)Ara(f), —O-Glc(2→1)Glc(2→1)Glc, —O-Glc(2→1)Glc(2→1)Xyl, —O-Glc(6→1)Glc(6→1)Xyl, —O-Glc(2→1)Glc(4→1)Xyl, —O-Glc(2→1)Lyx, —O-Glc(6→1)Lyx, —O-Glc(2→1)Glc(2→1)Rha, —O-Glc(2→1)Glc(2→1)Lyx, —O-Glc(2→1)Glc(2→1)Ara(f), —O-Glc(2→1)Glc(2→1)Ara(p), —O-Glc(2→1)Glc(6→1)Glc, —O-Glc(2→1)Glc(6→1)Rha, —O-Glc(2→1)Glc(6→1)Xyl, —O-Glc(2→1)Glc(6→1)Lyx, —O-Glc(2→1)Glc(6→1)Ara(f), —O-Glc(2→1)Glc(6→1)Ara(p), —O-Glc(6→1)Glc(2→1)Glc, —O-Glc(6→1)Glc(2→1)Rha, —O-Glc(6→1)Glc(2→1)Xyl, —O-Glc(6→1)Glc(2→1)Lyx, —O-Glc(6→1)Glc(2→1)Ara(f), —O-Glc(6→1)Glc(2→1)Ara(p), —O-Glc(6→1)Glc(6→1)Glc, —O-Glc(6→1)Glc(6→1)Rha, —O-Glc(6→1)Glc(6→1)Lyx, —O-Glc(6→1)Glc(6→1)Ara(f) or —O-Glc(6→1)Glc(6→1)Ara(p); wherein, Glc refers to glucopyranosyl, Xyl refers to xylopyranosyl, Rha refers to Rhamnopyranosyl, Ara(p) refers to arabinopyranosyl, Ara(f) refers to arabinofuranosyl, Lyx refers to Lyxosyl, number indicates carbon position, arrow (→) indicates the connection relationship, and the same hereinafter;

$R^{11}$ is a group formed by replacing one or more OH in $R^{10}$ with $R^{10}$, and each of the one or more than one $R^{10}$ groups independently can be the same as or different from each other.

$R^1$ is preferably hydroxy or

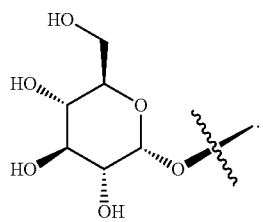

In Formula I, "*" represents a chiral carbon, that is preferably S-configuration.

The ginsenoside of Formula I is preferably

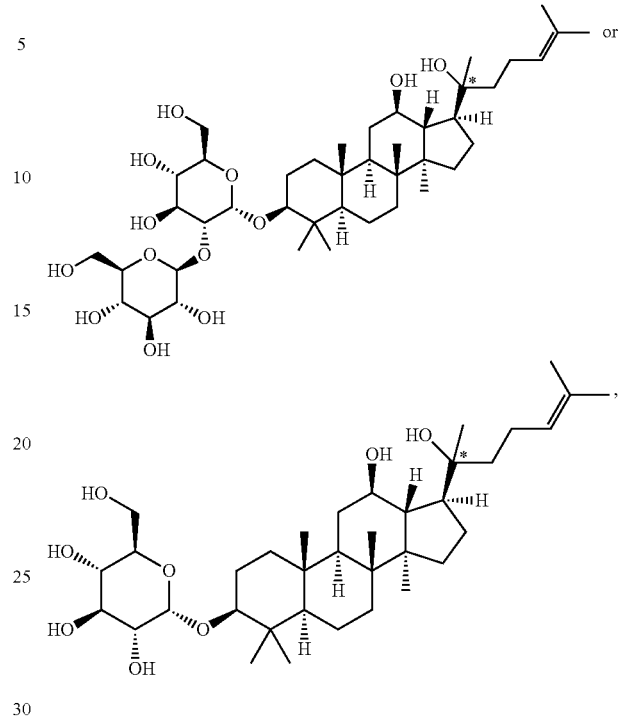

wherein, "*" represents a chiral carbon.

In the blank liposome of the present invention, the mean particle size of the blank liposome may be in the range of 20-500 nm, preferably 50-200 nm, more preferably 80-100 nm, most preferably 80-90 nm.

In the blank liposome of the present invention, the ginsenoside of Formula I is preferably micronized into ultra-fine powders before forming the thin film.

The mean particle size of the ultra-fine powders may be less than 50 μm, preferably less than 20 μm, more preferably less than 10 μm.

The micronization techniques used to process ginsenoside of formula I are conventional techniques in this field. Preferably, the micronization process is performed at 20-30° C. for around 20-40 min.

The purity of the ginsenoside of Formula I before forming the thin film may be equal or greater than 90%, preferably equal or greater than 95%, more preferably equal or greater than 98%, wherein the purity is analyzed by High Performance Liquid Chromatography (HPLC), and the percentage refers to the ratio of the peak area of ginsenoside of formula I to the total peak area in HPLC spectrum.

In the blank liposome of the present invention, encapsulation efficiency of the blank liposome is preferably greater than 90%, more preferably greater than 95%, most preferably greater than 98%.

In the blank liposome of the present invention, the mass ratio of lipid to ginsenoside of Formula I may be in the range of 0.5:1 to 100:1, preferably in the range of 2:1 to 20:1, more preferably in the range of 3:1 to 10:1, such as 5:1 or 7:1.

In the blank liposome of the present invention, the membrane can further comprise cholesterol.

When the blank liposome comprises cholesterol, then the mass ratio of the phospholipid to the ginsenoside of Formula I may be in the range of 0.5:1 to 100:1, preferably 2:1 to-20:1, more preferably 3:1 to 10:1. The mass ratio of cholesterol to the ginsenoside of Formula I may be in the range of 0.01:1 to 100:1, preferably 0.1:1 to 10:1, more preferably 0.5:1 to 2:1, such as 0.5:1.

When the blank liposome comprises cholesterol, then the mass percentage of the ginsenoside of Formula I in the membrane may be in the range of 1-50%, preferably 3-15%. The mass percentage of the lipid in the membrane is in the range of 30-90%, preferably 50-80%. The mass percentage of the cholesterol in the membrane may be in the range of 0-50%, preferably 0-10%; the percentage (%) refers to the ratio of the mass of each component to the total mass of the blank liposome.

In the blank liposome of the present invention, membrane of the blank liposome can further comprise a long-circulating material.

When the blank liposome comprises a long-circulating material, then the mass ratio of the lipid to the ginsenoside of Formula I may be in the range of 0.5:1-100:1, preferably 2:1-20:1, more preferably 3:1-10:1. The mass ratio of the long-circulating material to the ginsenoside of Formula I may be in the range of 0.01:1-10:1, preferably 0.1:1-5:1, more preferably 0.1:1-1:1.

Perferably, the blank liposome in the present invention can further comprise cryoprotectant, wherein the mass percentage of the cryoprotectant in the blank liposome may be the same as the percentage in the conventional liposome, such as less than 95% or 80%, preferably in the range of 0.5-70%, more preferably in the range of 5-60%, most preferably 30-60%; the percentage (%) refers to the ratio of the mass (i.e., weight) of cryoprotectant to the total mass of the blank liposome.

Perferably, the blank liposome in the present invention can further comprise antioxidant, wherein the mass percentage of the antioxidant in the blank liposome may be no more than 25%, preferably 0.001%-15%, more preferably 0.01%-10%, most preferably 0.01%-5% (such as 0.7%). The percentage (%) refers to the ratio of the mass (i.e., weight) of antioxidant to the total mass of the blank liposome.

Perferably, the blank liposome in the present invention can further comprise soybean oil and/or sodium oleate, wherein the mass percentage of the soybean oil and/or sodium oleate in the blank liposome may be in the range of 1-30%, preferably 1-20%, more preferably 1-10%, such as 7% or 8%. The percentage (%) refers to the ratio of the mass (i.e., weight) of soybean oil and/or sodium oleate to the total mass of the blank liposome. In this blank liposome, the mass ratio of the soybean oil and/or sodium oleate to the phospholipid may be in the range of 0.1:1-10:1, preferably 0.1:1-5:1, such as 0.12:1 or 0.14:1.

Perferably, the blank liposome in the present invention can further comprise other excipients, wherein the excipient is the conventional excipient in this field, such as surfactant, heat-sensitive excipient, a pH-sensitive material, and one or more ionic additives. In a preferred embodiment, the blank liposome in the present invention comprises components selected from the following groups: lipid and ginsenoside of Formula I; or lipid, ginsenoside of Formula I and cryoprotectant; or lipid, ginsenoside of Formula I and cholesterol; or lipid, ginsenosides of formula I, cholesterol and cryoprotectant; or lipid, ginsenoside of Formula I and long-circulating material; or lipid, ginsenoside of Formula I and antioxidants; or lipid, ginsenoside of Formula I, antioxidant and cryoprotectant; or lipid, ginsenoside of Formula I and soybean oil and/or sodium oleate; or lipid, ginsenoside of Formula I, cholesterol and long-circulating material; or lipid, ginsenoside of Formula I, cholesterol, long-circulating material and cryoprotectant; or lipid, ginsenoside of Formula I, cholesterol and antioxidants; or lipid, ginsenoside of Formula I, cholesterol, antioxidant and cryoprotectant; or lipid, ginsenoside of Formula I, cholesterol and soybean oil and/or sodium oleate; or lipid, ginsenoside of Formula I, cholesterol, long-circulating material and cryoprotectant; or lipid, ginsenoside of Formula I, cholesterol, cryoprotectant and soybean oil and/or sodium oleate; or lipid, ginsenoside of Formula I, cholesterol, cryoprotectant, long-circulating material and antioxidant; or lipid, ginsenoside of Formula I, cholesterol, cryoprotectant, long-circulating material and soybean oil and/or sodium oleate; or lipid, ginsenoside of Formula I, cholesterol, cryoprotectant, long-circulating material, antioxidant and soybean oil and/or sodium oleate.

In another preferred embodiment, the blank liposome comprises the above-mentioned components.

In a preferred embodiment, the blank liposome comprises ginsenoside of Formula I, lipid and cryoprotectant.

In a preferred embodiment, the blank liposome comprises lipid, ginsenoside of Formula I, antioxidant and cryoprotectant.

In a preferred embodiment, the blank liposome comprises lipid, ginsenoside of Formula I, cholesterol and cryoprotectant.

In a preferred embodiment, the blank liposome comprises lipid, ginsenoside of Formula I, cholesterol, soybean oil and/or sodium oleate, and cryoprotectant.

In a preferred embodiment, the blank liposome comprises lipid, ginsenoside of Formula I, cholesterol, long-circulating material, and cryoprotectant.

In a preferred embodiment, the blank liposome comprises lipid, ginsenoside of Formula I, cholesterol, antioxidant, long-circulating material, and cryoprotectant.

In a preferred embodiment, the blank liposome comprises lipid, ginsenoside of Formula I, cholesterol, antioxidant, soybean oil and/or sodium oleate, and cryoprotectant.

In the present invention, the lipid is the conventional lipid in this field, preferably refers to phospholipid, preferably one or more of the natural phospholipids, semisynthetic phospholipid and fully synthetic phospholipid.

In the present invention, the natural phospholipid preferably comes from soybean, egg yolk, brain or organ of animal, preferably comprises one or more of natural lecithin, sphingomyelin, glycerolphospholipid, soybean lecithin, egg lecithin and cephalin.

In the present invention, the semi-synthetic phospholipid or the fully synthetic phospholipid can be a conventional semi-synthetic phospholipid or fully synthetic phospholipid in this field, preferably consist of phospholipid of phosphatidylcholines (PC), phosphatidylserine (PS), phosphatidylinositol (PI), a phospholipid of phosphatidylethanolamine, phosphatidylglycerol (DSPG), dicetyl phosphate (DCP), a PEG-modified phospholipid, cholesteryl succinate (CHS) or 1-palmitoyl-2-oleoyl-sn-glycero-3-phosphocholine ((POPC) or 16:0 to 18:1 PC wherein 16:0 to 18:1 is in the format of (number of carbons in fatty acid chain): (number of double bonds in fatty acid chain)). Due to the heat-sensitivity of the semisynthetic or fully synthetic phospholipids, such as dipalmitoyl phosphatidylcholine (DPPC) and distearoylphosphatidylcholine (DSPC) etc., they can be used as heat-sensitive excipients at the same time.

In the present invention, the phospholipid of phosphatidylcholine can be a conventional phospholipid of phosphatidylcholine in this field, preferably comprises one or more of hydrogenated soybean phosphatidylcholine (HSPC), dipalmitoylphosphatidylcholine (DPPC), distearoylphosphatidylcholine (DSPC), dimyristoylphosphatidylcholine (DMPC), dilauroyl phosphatidylcholine (DLPC), dioleoylphosphatidylcholine (DOPC), phosphatidylcholine (PC), monopalmitoyl phosphatidylcholine (MPPC) or glycerophosphatidylcholine (GPC).

In the present invention, the phospholipid of phosphatidylethanolamine can be a conventional phospholipid of phosphatidylcholine in this field, preferably comprises one or more of 1-palmitoyl-2-oleoyl phosphatidylethanolamine (POPE), 1,2-dilauroy-sn-glycero-3-phosphatidylethanolamine (DLPE), dierucoyl phosphatidylethanolamine (DEPE), dioleoylphosphatidylethanolamine (DOPE), 1,2-di stearoyl-sn-glycero-3-phosphatidylethanolamine (DSPE), 1,2-Dipalmitoyl-sn-glycero-3-phosphatidylethanolamine (DPPE) or 1,2-Dimyristoyl-sn-glycero-3-phosphatidylethanolamine (DMPE).

In the present invention, the lipid is preferably egg lecithin, soybean lecithin, hydrogenated soybean lecithin or Lipoid S100 derived from soybean lecithin.

In the present invention, the long-circulating material can be a conventional PEG-modified phospholipid in this field, preferably comprises dimyristoyl Phosphoethanolamine (DMPE)-PEG (DMPE-PEG), dipalmitoyl phosphatidylethanolamine-PEG (DPPE-PEG), distearoyl phosphatidylethanolamine-PEG (DSPE-PEG), dioleoyl phosphatidylethanolamine-PEG (DOPE-PEG), C8 PEG ceramide (C8 ceramide-PEG), C16 PEG ceramide-(C16 ceramide-PEG), distearoyl phosphatidylethanolamine-PEG-succinyl (DSPE-PEG succinyl), distearoyl phosphatidylethanolamine-PEG-carboxyl (DSPE-PEG carboxylic acid), distearoyl phosphatidylethanolamine-PEG-maleimide (DSPE-PEG maleimide), distearoyl phosphatidylethanolamine-PEG-propionamide bis-mercaptopyridine (DSPE-PEG PDP), distearoyl phosphatidylethanolamine-PEG-cyanuric chloride (DSPE-PEG cyanur), distearoyl phosphatidylethanolamine-PEG-amino (DSPE-PEG amine), distearoyl phosphatidylethanolamine-PEG-biotin (DSPE-PEG biotin), distearoyl phosphatidylethanolamine-PEG-folate (DSPE-PEG folate), distearoyl phosphatidylethanolamine-PEG-folate (DSPE-PEG folate), dilauroyl phosphatidylethanolamine-PEG (DLPE-PEG), distearoyl phosphatidylethanolamine-PEG-active succinimidyl ester (DSPE-PEG-NHS), phosphatidylethanolamine-PEG-active succinimidyl ester (DMPE-PEG-NHS), dipalmitoyl phosphatidylethanolamine-PEG-active succinimidyl ester (DPPE-PEG-NHS), dilauroyl phosphatidylethanolamine-PEG-active succinimidyl ester (DLPE-PEG-NHS), distearoyl phosphatidylethanolamine-PEG-maleimide (DSPE-PEG-maleimide), Dimyristoyl phosphatidylethanolamine-PEG-maleimide (DMPE-PEG-maleimide), dipalmitoyl phosphatidylethanolamine-PEG-maleimide (DPPE-PEG-maleimide), dilauroyl phosphatidylethanolamine-PEG-maleimide(DLPE-PEG-maleimide), distearoyl phosphatidylethanolamine-PEG-biotin (DSPE-PEG-biotin), distearoyl phosphatidylethanolamine-PEG-fluorescein (DSPE-PEG-FITC), distearoyl phosphatidylethanolamine-PEG-hydroxyl (DSPE-PEG-OH), distearoyl phosphatidylethanolamine-PEG-amino (DSPE-PEG-NH2), phosphatidylethanolamine-PEG-amino (DMPE-PEG-NH2), dipalmitoyl phosphatidylethanolamine-PEG-amino (DPPE-PEG-NH2), dilauroyl phosphatidylethanolamine-PEG-amino(DLPE-PEG-NH2), distearoyl phosphatidylethanolamine-PEG-carboxyl (DSPE-PEG-COOH), dimyristoyl phosphatidylethanolamine-PEG-carboxyl (DMPE-PEG-COOH), dipalmitoyl phosphatidylethanolamine-PEG-carboxyl (DPPE-PEG-COOH), dilauroyl phosphatidylethanolamine-PEG-carboxyl (DLPE-PEG-COOH), distearoyl phosphatidylethanolamine-PEG-thiol (DSPE-PEG-SH), distearoyl phosphatidylethanolamine-PEG-silane (DSPE-PEG-silane), distearoyl phosphatidylethanolamine-PEG-azide (DSPE-PEG-N3), cholesterol-PEG (cholesterol PEG), methoxy-PEG-cholesterol (mPEG-CLS), cholesterol-PEG-active succinimidyl ester (cholesterol PEG NHS ester), cholesterol-PEG-maleimide (CLS-PEG-Mal), cholesterol-PEG-biotin (cholesterol PEG biotin), cholesterol-PEG-fluorescein (cholesterol PEG fluorescein), cholesterol-PEG-carboxyl (cholesterol PEG COOH), cholesterol-PEG-amino (cholesterol-PEG-NH2) or cholesterol-PEG-thiol (Cholesterol-PEG-SH). The number average molecular weight of the above-mentioned PEG is preferably in the range of 300 to 50000, more preferably in the range of 500 to 10000, e.g. at about 300, 350, 500, 550, 1000, 2000, 3400, 5000, 10000, 20000, 30000, 40000 or 50000.

In the present invention, the number average molecular weight of DMPE-PEG is preferably 350, 550, 750, 1000, 2000, 3000 or 5000. The number average molecular weight of DPPE-PEG is preferably 350, 550, 750, 1000, 2000, 3000 or 5000. The number average molecular weight of DSPE-PEG is preferably 350, 550, 750, 1000, 2000, 3000, 5000, 10000, 20000, 30000 or 40000. The number average molecular weight of DOPE-PEG is preferably 350, 550, 750, 1000, 2000, 3000 or 5000. The number average molecular weight of C8 Ceramide-PEG is preferably 750, 2000 or 5000. The number average molecular weight of DLPE-PEG is preferably 2000 or 5000. The number average molecular weight of DSPE-PEG-NHS is preferably 1000, 2000, 5000, 10000, 20000, 30000 or 40000. The number average molecular weight of DMPE-PEG-NHS is preferably 3400 or 5000. The number average molecular weight of DPPE-PEG-NHS is preferably 3400 or 5000. The number average molecular weight of DLPE-PEG-NHS is preferably 3400 or 5000. The number average molecular weight of DSPE-PEG-Maleimide is preferably 1000, 2000, 3400, 5000 or 10000. The number average molecular weight of DMPE-PEG-Maleimide is preferably 1000, 2000, 3400, 5000 or 10000. The number average molecular weight of DPPE-PEG-Maleimide is preferably 1000, 2000, 3400, 5000 or 10000. The number average molecular weight of DLPE-PEG-Maleimid is preferably 1000, 2000, 3400, 5000 or 10000. The number average molecular weight of DSPE-PEG-Biotin is preferably 1000, 2000, 3400, 5000 or 10000. The number average molecular weight of DSPE-PEG-FITC is preferably 1000, 2000, 3400, 5000 or 10000. The number average molecular weight of DSPE-PEG-OH is preferably 2000, 3400 or 5000. The number average molecular weight of DSPE-PEG-NH$_2$ is preferably 2000, 3400 or 5000. The number average molecular weight of DMPE-PEG-NH$_2$ is preferably 2000, 3400 or 5000. The number average molecular weight of DPPE-PEG-NH$_2$ is preferably 2000, 3400 or 5000. The number average molecular weight of DLPE-PEG-NH$_2$ is preferably 2000, 3400 or 5000. The number average molecular weight of DSPE-PEG-COOH is preferably 2000, 3400 or 5000. The number average molecular weight of DMPE-PEG-COOH is preferably 2000, 3400 or 5000. The number average molecular weight of DPPE-PEG-COOH is preferably 2000, 3400 or 5000. The number average molecular weight of DLPE-PEG-COOH is preferably 2000, 3400 or 5000. The number average molecular weight of DSPE-PEG-SH is preferably 5000. The number average molecular weight of DSPE-PEG-Silane is preferably 3400. The number average molecular weight of DSPE-PEG-N3 is preferably 2000, 3400 or 5000. The number average molecular weight of mPEG-CLS is preferably 1000, 2000, 5000, 10000 or 20000. The number average molecular weight of Cholesterol PEG NHS ester is preferably 1000, 2000, 3400, 5000 or 10000. The number average molecular weight of CLS-PEG-Mal is preferably 2000, 3400, 5000 or 10000. The number average molecular weight of CLS-PEG-Biotin is preferably 2000, 3400 or 5000. The number average molecular weight of CLS-PEG- FITC is preferably 2000, 3400 or 5000. The number average molecular weight of Cholesterol PEG COOH is preferably 3400. The number average molecular weight of Cholesterol PEG amine is preferably 3400. The number average molecular weight of Cholesterol PEG Thiol/Sulfhydril is preferably 3400.

In the present invention, the long-circulating material is preferably PEG2000-DSPE.

In the present invention, the antioxidant can be a conventional antioxidant in this field, preferably comprises one or more of compounds selected from the group consisting of sodium metabisulfite, sodium thiosulfate, propyl gallate, ascorbic acid, α-tocopherol, α-hydroxyl acid, flavonoid, phenylpropanoids, vitamin E, vitamin C, fumaric acid, cysteine, methionine, butylhydroxyanisole (BHA), butylated hydroxytoluene (BHT), thiodipropionic acid, sulfites (e.g., sodium sulfite), hydrosulphite (e.g., sodium hydrosulfite), dithio aminobenzoic acid, citric acid, malic acid, sorbitol, glycerol, propylene glycol, hydroquinone, hydroxycoumarin, ethanolamine, phosphoric acid or phosphorous acid.

In the present invention, the antioxidant is preferably vitamin E, vitamin C, sodium thiosulfate, or sodium sulfite.

In the present invention, the cryoprotectant can be a conventional cryoprotectant in this field, comprising one or more of sugars, polyols, amino acids and buffering agents. Wherein, the sugar is preferably one or more of monosaccharides, disaccharides and polysaccharides. The monosaccharides are preferably one or more of glucose, mannitol, xylitol and sorbitol. The disaccharides are preferably one or more of sucrose, lactose, galactose and maltose. The polysaccharide is preferably trehalose. The polyols are preferably propanediol and/or propanediol. The amino acids are preferably α-amino acids, such as one or more of threonine, glycine, glutamic acid, arginine, and histidine. The buffer preferably refers to a buffer solution. The buffer solution can be a conventional buffer solution in this field with pH in the range of 3-10, and preferably 5-7. The buffer solution is preferably an aqueous solution of ammonium sulfate, an ethanol-acetic acid buffer solution, a tris(hydroxymethyl) aminomethane (Tris) buffer solution, a barbital buffer solution, a sodium formate buffer solution, a phthalate buffer solution, an citrate buffer solution, a citric acid-disodium hydrogen phosphate buffer solution, an ammonia-ammonium chloride buffer solution, a borax-calcium chloride buffer solution, an acetate buffer solution, an lithium acetate buffer solution, sodium acetate buffer solution, an ammonium acetate buffer, a triethylammonium phosphate buffer (TEAP) or phosphate-buffered saline (PBS).

In the present invention, the cryoprotectant is preferably an aqueous solution of trehalose, glucose, sucrose, propaneldiol, propylene glycol, xylitol or ammonium sulfate.

In the present invention, the surfactant is preferably polyethylene glycol (PEG), and/or polysorbate. Wherein the number average molecular weight of PEG is preferably in the range of 200-8000. The polysorbate preferably comprises one or more of polyoxyethylenesorbitan monolaurate, polyoxyethylenesorbitan monopalmitate, polyoxyethylenesorbitan monostearate, polyoxyethylenesorbitan trioleate, PEG-phosphatidylethanolamine, PEG-polylactic acid (PEG-PLA), poly L-lysine-poly(lactic-co-glycolic) acid, polyetherimide-polylactic acid, PEG-polycaprolactone (PEG-PCL), PEG-poly(lactic-co-glycolic) acid (PEG-PLGA), PEG-poly hexadecyl cyanoacrylate (PEG-PHDCA), poloxamer 188 (Pluroic® F-68), polyoxyethylene fatty acid ester (Mrij series), polyoxyethylene fatty acid ether (Brij series), or polyoxyethylene castor oil ether.

In the present invention, the heat-sensitive excipient comprises a polymer and/or a surfactant which brings heat-sensitivity to the liposome. The polymer preferably comprises one or more of polyproplylene acrylamide, polypropylene acrylic acid, polyphoester, or poly(ester amide) copolymer. The surfactant is preferably a Tween surfactant (such as Tween-80) and/or a brij surfactant.

In the present invention, the ionic additive preferably comprises a cationic additive (such as octadecylamine) or an anionic additive (such as phosphatidic acid and/or phosphatidylserine).

In the present invention, mass percentage of the above-mentioned excipients can be the mass percentage of such excipients in the conventional liposomes in this field. Wherein the blank liposome contains a surfactant, mass percentage of the surfactant in the blank liposome is preferably in the range of 0-50%, excluding 0%. Wherein the blank liposome contains an ionic additive, mass percentage of the ionic additive in the blank liposome is preferably in the range of 0-10%, excluding 0%.

The present invention also provides a preparation method of the said blank liposome with ginsenoside of Formula I as membrane materials.

In the present invention, the blank liposome can be prepared using conventional methods in this filed. Preparation of the blank liposome comprises an ethanol or ether injection method, reverse phase evaporation method, freeze-thawed method, double emulsion method, initiative encapsulation method, precursor liposome preparation method, film dispersion method, freeze-drying method, ammonium sulfate gradient method or pH gradient method, or any combination of the above-mentioned methods. The present invention preferably adopts the following steps:

Step (1): mix a lipid and a ginsenoside of Formula I in an organic solvent to obtain a clear solution, optionally with a cholesterol, a long-circulating material, a hydrophobic antioxidant, a soybean oil and/or sodium oleate, a hydrophobic surfactant, a hydrophobic heat-sensitive excipient, a hydrophobic pH sensitive material, and/or a hydrophobic ionic additive; The organic solvent is one or more solvents selected from alcohol, halogenated hydrocarbon and nitrile solvent. The ginsenoside of Formula I is micronized into ultra-fine powder with the average particle size no more than 50 μm.

Step (2): remove the organic solvent from the clear solution obtained in step (1), after film-formation, mix the film with an aqueous solution containing a cryoprotectant, optionally with a hydrophilic antioxidant, a hydrophilic surfactant, a hydrophilic heat-sensitive excipient, a hydrophilic pH sensitive material, and/or a hydrophilic ionic additive. After sonication or high pressure homogenization, the mixture is passed through a membrane filter to obtain an aqueous solution that containing the blank liposome. Freeze-dry the aqueous solution to obtain the said blank liposome.

The lipid, the ginsenoside of formula I, the cholesterol, the long-circulating material, the hydrophobic antioxidant, the soybean oil and/or sodium oleate, the hydrophobic surfactants, the hydrophobic heat sensitive excipient, the hydrophobic pH-sensitive material, the hydrophobic ionic additive and the micronization of ginsenoside of Formula I are as same as above defined.

In step (1), the halogenated hydrocarbon solvent is $C_{1-4}$ halogenated hydrocarbon solvent, preferably $C_{1-2}$ halogenated hydrocarbon solvent, more preferably chloroform, dichloromethane and dichloroethane, most preferably one or more of dichloromethane and chloroform. The alcohol solvent is $C_{1-4}$ alcohol solvent, preferably $C_{1-3}$ alcohol solvent, and more preferably one or more of methanol, ethanol, n-propanol, isopropanol and n-butanol, most preferably methanol, ethanol or isopropanol. The nitrile solvent is acetonitrile. When the halogenated hydrocarbon solvent is mixed with the alcohol solvent, then the volume ratio of the halogenated hydrocarbon solvent to the alcohol solvent is in the range of 5:1-100:1, preferably 5:1-10:1. When the organic solvent is a mixture of the halogenated hydrocarbon solvent and the nitrile solvent, then the volume ratio of the halogenated hydrocarbon solvent to the nitrile solvent is in the range of 5:1-100:1, preferably 5:1-10:1. The amount of the solvent can be the same amount used in preparation of conventional liposome in this field, generally, the required volume should be able to completely dissolve all the materials. Preferably, the ratio of the volume of the said organic solvent to the mass of all the components in step (1) is in the range of 5-200 mL/g. In step (1), the average particle size of the micronized ginsenoside of Formula I is no more than 20 μm, preferably no more than 10 μm.

In step (1), the mixing temperature is the temperature conventionally used in this field in the range of 0-80° C., preferably 20-80° C., more preferably 40-65° C. According to the general knowledge in this field, it requires heating to reach a mixing temperature of 80° C. Or when there is a temperature-sensitive substance except cryoprotectant, such as protein, the mixing temperature is below 0° C.

In step (2), the removal of the organic solvent from the clear solution obtained from step (1) is conducted with a rotary evaporator or a film evaporator, choice of the temperature is based on the property of the organic solvent needed to be removed, generally in the range of 40-65° C.

In step (2), sonication, high pressure homogenization or membrane filtration is a conventional process in this field. After these processes, the average particle size is in the range of 0.05-0.3 μm, preferably 0.05-0.2 μm.

In step (2), the filtration is a conventional method used in preparation of liposomes in this field. The purpose of filtration is to remove bacteria, solid particles, and larger size liposomes (Non-encapsulated drugs can also be removed in the preparation of liposome loaded with active substance.). In the present invention, the filtration is preferably a microporousmembrane filtration. Preferably, the pore size of the microporous membrane is 0.22 micron.

In step (2), the aqueous cryoprotectant solution refers to an aqueous solution formed by mixing the cryoprotectant and water. The aqueous cryoprotectant is preferably an aqueous solution with 5-10% cryoprotectant, the percentage is a mass percentage, referring to the ratio of the mass of the cryoprotectant to the total mass of the aqueous solution. The amount of the aqueous cryoprotectant is not limited to particular numbers, as long as it does not affect the formation of the blank liposome.

In step (2), the drying process can be a conventional process in this field, preferably freeze-drying which generally utilize a freeze dryer under vacuum. The temperature and time required by the freeze-drying process are the conventional temperature and time in this field without particular limitation.

In step (2), for easy storage, the aqueous solution of the blank liposome obtained from step (2) is aliquoted into vials, dried and sealed inside the vial with protective gas (argon or nitrogen).

The present invention also provides a blank liposome preparation method with ginsenoside of formula I as membrane material.

The present invention further provides a liposome loaded with active substance, comprising a blank liposome with ginsenoside of formula I as membrane material and active substance encapsulated within the membrane.

The average particle size of the blank liposome loaded with active substance can be a conventional particle size in this field, preferably 30-500 nm, more preferably 30-300 nm, most preferably 50-200 nm.

The encapsulation efficiency of the loaded liposome may be more than 80%, preferably more than 90%, more preferably over 95%.

In the present active substance-loaded liposome, when the active substance is a drug, then the drug-loaded liposome can be administrated in a conventional way in this field, preferably by injection, oral administration or cutaneous penetration, for the treatment of diseases and/or medical health care. Therefore, the liposome loaded with active substance is generally prepared in the form suitable for injection, lyophilized powder injection, oral administration, topical administration or pulmonary (by inhalation) administration. The injection administration preferably includes intravenous injection, intramuscular injection, intraperitoneal injection, intradermal injection or subcutaneous injection. Preferably, the injection solution is prepared by rehydrating the loaded liposome with phosphate-buffered saline (PBS) or 5% aqueous glucose solution.

In the loaded liposome of the present invention, when the active substance is an anti-tumor drug, then the loaded liposome preferably has long-circulating properties. In the loaded liposome, the mass ratio of the active substance to the ginsenoside of formula I is in the range of 0.1:1-10:1, preferably 0.5:1-2:1 (such as 0.5:1 or 1).

In the loaded liposome of the present invention, the loaded active substance can be a conventional drug in this field, preferably comprising one or more anti-tumor drugs.

In the loaded liposome of the present invention, the loaded antitumor drug can be a conventional anticancer drug in this field, preferably comprising one or more drugs selected from paclitaxel, docetaxel, cabazitaxel, tesetaxel, ortataxel, larotaxel, simotaxel, irinotecan hydrochloride, hydroxycamptothecin, aminocamptothecin, 7-ethyl-10-hydroxycamptothecin, cisplatin, carboplatin, oxaliplatin, harringtonine, homoharringtonine, triptolide, cytarabine, etoposide phosphate, desoxypodophyllotoxin, huperzine-A, vinorelbine tartrate, vincristine sulfate, vinblastine sulfate, epothilone A, epothilone B, epothilone C, epothilone D, epothilone E, epothilone F, decitabine, arsenic trioxide ($As_2O_3$), all-trans retinoic acid, Azithromycin, daunorubicin, pingyangmycin, doxorubicin hydrochloride, idarubicin hydrochloride.

In a preferred embodiment, the active substance is paclitaxel, docetaxel, irinotecan, doxorubicin or cisplatin.

The present invention also provides a preparation method of the active substance-loaded liposome with the following steps:

Step (1): mix the lipid, the ginsenoside of Formula I and the active substance in an organic solvent to obtain a clear solution, optionally with a cholesterol, a long-circulating material, a hydrophobic antioxidant, soybean oil and/or sodium oleate, a hydrophobic surfactant, a hydrophobic heat-sensitive excipient, a hydrophobic pH sensitive material, and/or a hydrophobic ionic additive, wherein the solvent is one or more of alcohol, halogenated hydrocarbon and nitrile solvent. The ginsenoside of formula I is micronized to superfine powder with an average particle size no more than 50 μm.

Step (2): remove the organic solvent in the clear solution obtained from step (1), after film formation, optionally hydrate the film with an aqueous solution containing a cryoprotectant, and optionally with one or more additives comprising a hydrophilic antioxidant, a hydrophilic surfactant, a hydrophilic heat-sensitive excipient, a hydrophilic pH sensitive material, and/or a hydrophilic ionic additive. After sonication or high-pressure homogenization, the mixture is passed through a membrane to obtain an aqueous solution containing the active substance-loaded liposome, then freeze-dry the aqueous solution to obtain the loaded liposome.

The conditions and parameters of preparation of the loaded liposome are the same as the preparation of the blank liposome in step (1).

In step (2), the cryoprotectant can be added after the aqueous solution of the active substance-loaded liposome is obtained.

In the preparation of the liposome loaded with active substance, the amount of the active substance used for the preparation can be the amount conventionally used in this field. The mass ratio of the active substance to the ginsenoside of formula I is in the range of 0.1-10:1, preferably 0.5-2:1, such as 0.5:1 and 1.

The present invention provides a liposome loaded with active substance prepared by the preparation method discussed above.

In the present invention, the encapsulation efficiency (EE %) refers to the mass percentage of the encapsulated active substance to the total mass of the active substance and is calculated according the formula: EE %=$(1-C_f/C_t) \times 100\%$, wherein $C_f$ is the mass of the free drug and $C_t$ is the total mass of the loaded drug in liposomes. This analysis method is the conventional method in this field.

In the present invention, the "S configuration" is a term referring to the R/S nomenclature system for a chiral carbon atom. The definition of R/S nomenclature system is as follows: a, b, c and d respectively represent the chemical groups attached to a central carbon. When a, b, c and d are different groups, the molecule is chiral. According to the CIP priority rules, the four substituents in the molecule are arranged in an order of a>b>c>d. The smallest group d is placed farthest away from the observer, and the other groups are observed in the order of a to b to c. If a to b and then to c (a→b→c) is clockwise, the configuration of the center carbon is defined as R (Latin rectus), otherwise it is S (Latin sinister).

In the present invention, room temperature refers to 10-30° C.

In the present invention, the density of the cryoprotectant aqueous solution or the active substance aqueous solution is considered as 1 g/mL (i.e. water density). Therefore, the total mass of the cryoprotectant aqueous solution or the active substance aqueous solution is calculated according to the formula: $m = \rho \times V$.

In the present invention, density of the organic solution containing the active substance is considered same as the density of the organic solvent itself, for example, when the organic solvent is DMSO, the density of the organic solution containing the active substance is 1.1 g/mL.

In the present invention, the term "hydrophilic antioxidant" refer to some antioxidants that can be dissolved in water, preferably ascorbic acid, isoascorbic acid and its salts, phytic acid, and amino acids. The water-soluble antioxidants are included in the the above-mentioned antioxidants. The prominent function of hydrophilic antioxidant is to mask the catalytic oxidation ions and avoid color changing and browning of fruits and vegetables, and have an auxiliary and reinforcing effect to the lipophilic antioxidants added to the water containing oil or emulsified food.

In the present invention, the term "hydrophilic surfactant" refers to a surfactant that can be dissolved in water, such as polysorbitol ester. The water-soluble surfactant is included in the above-mentioned surfactant.

In the present invention, the term "hydrophilic heat-sensitive exciperant" refers to a water-soluble surfactant that is sensitive to the temperature, such as Tween surfactants. The hydrophilic heat-sensitive excipients are included in the heat-sensitive excipients.

In the present invention, the term "hydrophilic pH sensitive substance" refers to a water-soluble surfactant that is sensitive to the pH value. The hydrophilic pH-sensitive substances are included in the pH-sensitive substances.

In the present invention, the term "hydrophilic ionic additive" means that the ions in such ionic additive are hydrophilic ions. The hydrophilic ionic additive is included in the ionic additive.

In the present invention, in some preferred embodiments, the above-mentioned conditions can be optionally combined according to the general knowledge in this field.

The reagents and raw materials used in the present invention are commercially available.

The advantages of present invention are as follows: Ginsenoside Rg3 or Rh2 in the present invention displays anti-tumor activity and can be used as membrane material. The disclosed liposome with Rg3 or Rh2 as membrane materials meet the requirements in the aspects of hemolysis, film-forming property and drug stability. The blank liposome with ginsenoside as multifunctional membrane material in the present invention has advantages in high efficiency, good safety, good stability, prolonged circulation time, good uniformity, good stability and reliable quality, and convenient preparation methods. The blank liposome in the present invention can encapsulate active substance to obtain a loaded liposome. When the active substance is an antitumor drug, the drug-loaded liposome generally has long-circulating time, and stronger drug efficacy.

BRIEF DESCRIPTION OF THE DRAWINGS

FIG. 5S is a fluorescence ruler, wherein color is red, yellow, green and blue in a sequence indicating the fluorescence intensity from the strongest to the weakest; FIGS. 5-B1-B5, 5-C1-C5, 5-D1-D5 are respectively the fluorescence distribution of the corresponding groups at the $2^{nd}$, $4^{th}$, $8^{th}$, $12^{th}$ and $24^{th}$ hour, and FIG. 5-B1-B5 are IR-783-Rg5-Gipo group, FIG. 5-C1-C5 are IR-783-Rh2-Gipo group, FIG. 5-D1-D5 are IR-783-Rg3-Gipo group.

FIG. 6-S is a fluorescence ruler, wherein color is red, yellow, green and blue in a sequence indicating the fluorescence intensity from the strongest to the weakest and FIG. 6-A, FIG. 6-B, FIG. 6-C and FIG. 6-D are respectively the control group, IR-783-Rg5-Gipo group, IR-783-Rg3-Gipo group and IR-783-Rh2-Gipo group.

FIG. 14 is the cell survival rate of human gastric cancer cells (BGC-823) with addition of Rg5 group, Rg3 group, Rh2 group, Rg5-blank group, Rg3-blank group, Rh2-blank group, PTX group, PTX-Cho-Lipo group, PTX-Rg5-Gipo group, PTX-Rg3-Gipo group and PTX-Rh2-Gipo group in.

DETAILED DESCRIPTION OF THE PREFERRED EMBODIMENT

Figure 1:
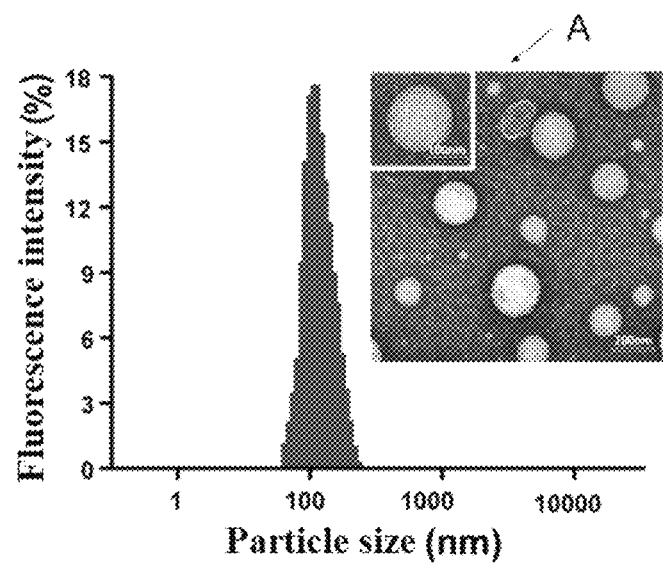
FIG. 1 is the particle size distribution of the liposome loaded with paclitaxel and cholesterol, wherein A is the electron microscope image showing the particle size of the liposome loaded with paclitaxel and cholesterol.

The following examples further illustrate the present invention, but the present invention is not limited thereto.

Below presents preferred embodiments of the present invention based on the drawings in order to illustrate the technical schemes of the present invention in detail.

1. Experimental drugs: 20(S)-ginsenoside Rg3, 20(R)-ginsenoside Rg3, 20(S)-ginsenoside Rh2, 20(R)-ginsenoside Rh2 are commercially available in this field, such as Shanghai Ginposome PharmaTech Co., Ltd., Suzhou Star Ocean Ginseng Bio-pharmaceutical Co., Ltd., and/or Shanghai Yuanye Bio-Technology Co., Ltd.

2. Experimental Instruments: The instruments used in the following embodiments are self-owned by Shanghai Ginposome PharmaTech Co., Ltd., the model and supply information of the instruments are listed as follows:

Ultra-Micro Pulverizer (ZD-10S, Shanghai Lvyi Machinery Manufacturing Co., Ltd.)

High performance liquid chromatography (Agilent 1100), Alltech 3300ELSD detector, Anjielun Technology China Co., Ltd.

Rotary evaporator (ZX98-1 5L), Shanghai Looyesh Instrument Co., Ltd.;

20 L Rotary evaporator (R5002K), Shanghai Xiafeng Instrument Factory;

Lyophilizer (FD-1D-80), Shanghai Bilang Instrument Manufacturing Co. Ltd.;

Lyophilizer (PDFD GLZ-1B), Shanghai Pudong Freeze dryer Equipment Co., Ltd.)

Precision weighing balance (CPA2250 0.00001 g Readability), Sartorius (Shanghai) Trade Co., Ltd.;

Electronic balance (JY3003 0.001 g Readability), Shanghai Shunyu Hengping Science Instrument Co. Ltd.).

3. The present invention is further explained by the following embodiments, but not limited to the following embodiments. The experimental methods without giving specific conditions, are carried out by conventional methods and conditions used in this field, or according to commodity specifications. The temperature and pressure preferably refer to room temperature of 10 to 30° C. and standard atmosphere pressure if not specified. Reflux temperature, if not specified, is defined by the solvent used.

Ultrafine Powder Process

To get the ginsenoside Rg3 ultrafine powder, 500 g ginsenoside Rg3 is dried to water content less than 1% and crushed by Ultra-Micro Pulverizer ZD-10S for 30 min. During the process, the inside temperature of pulverizer chamber is maintained at 20-30° C. with a cooled circulating water. The average size of more than 90% particles is less than 10 μm measured by electron microscope.

The Preparation of the Liposomes

Embodiment 1

The Preparation of a Conventional Rg3 Liposome

A mixture of Egg lecithin 1 g, cholesterol 0.1 g and ginsenoside 20(S)-Rg3 (without ultra-micro pulverization) 0.1 g were added to 20 mL anhydrous ethanol and stirred at room temperature to form a clear solution. Then the organic solvent was removed by a rotary evaporator in a thermostatic water bath at 40 to 50° C. The formed thin film was hydrated with 20 mL 5% trehalose aqueous solution (the percentage refers to the ratio of the mass of the trehalose to the total mass of the trehalose aqueous solution). The suspension was then sonicated until the particle size of the liposome was between 0.1 and 0.3 micron. After sonication, the liposome suspension was passed through a 0.22-micron microporous membrane to obtain an aqueous solution of ginsenoside Rg3 liposome. Then the aqueous solution was aliquoted into vials and placed in a freeze-dryer to lyophilization for 72 hours. The conventional Rg3 liposome was obtained and sealed in the vial by a protective gas (argon or nitrogen). By calculation, D10 of the liposome was 75 nm, D50 was 118 nm, D90 was 131 nm. As hereinafter, D10, D50, and D90 describe diameter, where 10%, 50%, and 90% of particle size distribution were under the reported particle size.

Embodiment 2

The Preparation of Rg3 Blank Liposome

Egg lecithin 1 g and ginsenoside 20(S)-Rg3 ultrafine powder 0.1 g were added to 200 mL chloroform and stirred to form a clear solution at room temperature. The organic solvent was removed by a rotary evaporator in a thermostatic water bath at 40 to 50° C. to form a film. The formed thin film was hydrated with 20 mL 5% trehalose aqueous solution (the percentage refers to the ratio of the mass of the trehalose to the total mass of the trehalose aqueous solution). The liposome suspension was sonicated until the particle size of the liposome was between 0.1 and 0.3 micron. Then the suspension was passed through a 0.22-micron microporous membrane to obtain an aqueous solution of ginsenoside Rg3 liposome. Then the aqueous solution was aliquoted into vials and placed in a freeze-dryer to for 72 hours. After lyophilization, the obtained Rg3 blank liposome was sealed in the vial by a protective gas (argon or nitrogen). By calculation, the D10 of the liposome was 66 nm, D50 was 90 nm, D90 was 105 nm.

Embodiment 3

The Preparation of Rg5 Blank Liposome

In accordance with the method in embodiment 2, the Rg5 Blank liposome was prepared by replacing Rg3 with Rg5. After evaluation, the D10 of the liposome was 70 nm, D50 was 96 nm and D90 was 111 nm.

Embodiment 4

The Preparation of Rg3 Blank Liposome

Egg lecithin 0.5 g, ginsenoside 20(R)-Rg3 ultrafine powder 0.1 g and Vitamin E 0.1 g were added into 200 mL dichloromethane and stirred to form a clear solution at room temperature. The organic solvent was removed by a rotary evaporator in a thermostatic water bath at 40 to 50° C. to form a film. The formed thin film was hydrated with 20 mL 5% glucose aqueous solution (the percentage refers to the ratio of the mass of the glucose to the total mass of the glucose aqueous solution). The liposome suspension was sonicated until the particle size of the liposome was between 0.1 and 0.3 micron. Then the suspension was passed through a 0.22-micron microporous membrane to obtain an aqueous solution containing ginsenoside Rg3 liposome. Then the aqueous solution was aliquoted into vials and placed in a freeze-dryer to for 72 hours. After lypholization, the obtained Rg3 blank liposome was sealed in the vial by a protective gas (argon or nitrogen). By calculation, the D10 diameter of the liposome was 88 nm, D50 was 116 nm, D90 was 153 nm.

Embodiment 5

The Preparation of Rg3 Blank Liposome

Soybean lecithin 0.6 g and ginsenoside 20(S)-Rg3 ultra-fine powder 0.2 g were added into 200 mL chloroform/methanol (1:1, v/v) and stirred to form a clear solution at room temperature. The organic solvent was removed by a rotary evaporator in a thermostatic water bath at 50 to 60° C. to form a film. The formed thin film was then hydrated with 20 mL 5% sucrose aqueous solution (the percentage refers to the ratio of the mass of the sucrose to the total mass of the sucrose aqueous solution) and then sonicated until the particle size of the liposome was between 0.1 and 0.3 micron. The liposome suspension was passed through a 0.22-micron microporous membrane to obtain an aqueous solution containing ginsenoside Rg3 blank liposome. Then the aqueous solution was aliquoted into vials and placed in a freeze-dryer for 72 hours. After lyophilization, the obtained Rg3 blank liposome was then sealed by a protective gas (argon or nitrogen). By calculation, the D10 of the liposome was 60 nm, D50 was 84 nm, D90 was 102 nm.

Embodiment 6

The Preparation of Rh2 Blank Liposome

Hydrogenated soybean lecithin (HSPC) 0.7 g, ginsenoside 20(S)-Rh2 ultrafine powder 0.1 g and cholesterol 0.2 g were added into 200 mL chloroform and stirred to form a clear solution at room temperature. The organic solvent was removed by rotary evaporation in a thermostatic water bath at 60° C. to 65° C. to form a film. The formed film was hydrated using 20 mL 5% mannitol aqueous solution (the percentage refers to the ratio of the mass of the mannitol to the total mass of the mannitol aqueous solution) and then sonicated until the particle size of the liposome was between 0.1 and 0.3 micron to obtain an aqueous solution of ginsenoside Rh2 blank liposome. Then the obtained aqueous solution was aliquoted into vials and placed in a freeze-dryer to lyophilization for 72 hours. Then the obtained Rh2 blank liposome was sealed in the vial by a protective gas (argon or nitrogen). By calculation, the D10 of the liposome was 94 nm, D50 was 120 nm, D90 was 133 nm.

Embodiment 7

The Preparation of Rh2 Blank Liposome

Egg lecithin 0.4 g, ginsenoside 20(R)-Rh2 ultra-fine powder 0.1 g, soybean oil 0.2 g and vitamin C 0.1 g were added into 200 mL chloroform/isopropyl alcohol(9:1 v/v) and stirred to form a clear solution at room temperature. The organic solvent was removed by rotary evaporation in a thermostatic water bath at 60° C. to 65° C. to form a film. The formed film was hydrated with 20 mL 5% propanediol aqueous solution (the percentage refers to the ratio of the mass of the propanediol to the total mass of the propanediol aqueous solution) and sonicated until the particle size of the liposome was between 0.1 and 0.3 micron. After sonication, the liposome suspension was passed through a 0.22-micron microporousmembrane to obtain an aqueous solution of ginsenoside Rh2 blank liposome. Then the aqueous solution was aliquoted into vials and placed in a freeze-dryer to lyophilization for 72 hours. Then the obtained Rh2 blank liposome was sealed in the vial by a protective gas (argon or nitrogen). By evaluation, the D10 diameter of the liposome was 124 nm, D50 was 157 nm, D90 was 189 nm.

Embodiment 8

The Preparation of Rg3 Blank Liposome

Egg lecithin 0.9 g, ginsenoside 20(S)-Rg3 ultrafine powder 0.2 g and PEG2000-DSPE 0.05 g were mixed with 200 mL chloroform/methanol (1:1, v/v) and stirred to form a clear solution at room temperature. The organic solvent was removed by rotary evaporation in a thermostatic water bath at 55 to 65° C. to form a film. The formed film was hydrated with 20 mL 5% glycerol aqueous solution (the percentage refers to the ratio of the mass of the glycerol to the total mass of the glycerol aqueous solution) and sonicated until the particle size of the liposome was between 0.1 and 0.3 micron. After sonication, the liposome suspension was passed through a 0.45-micron microporous membrane filter to obtain an aqueous solution of ginsenoside Rg3 blank liposome. Then the aqueous solution was aliquoted into vials and placed in a freeze-dryer to lyophilization for 72 hours. Then the obtained Rg3 blank liposome was sealed in the vial by protective gas (argon or nitrogen). By calculation, the D10 diameter of the liposome was 62 nm, D50 was 71 nm, D90 was 85 nm.

Embodiment 9

The Preparation of Rg3 Blank Liposomes

Soybean lecithin S100 0.9 g, ginsenoside 20(S)-Rg3 ultrafine powder 0.2 g, Vitamin E 0.01 g, cholesterol 0.1 g and mPEG2000-DSPE 0.05 g were mixed with 20 mL chloroform/acetone (1:1 v/v) and stirred to form a clear solution at room temperature. The organic solvent was removed by rotary evaporation in a thermostatic water bath at 45° C. to 55° C. to form a film. The formed film was hydrated with 20 mL 5% galactose aqueous solution (the percentage refers to the ratio of the mass of the galactose to the total mass of the galactose aqueous solution) and sonicated until the particle size of the liposome was between 0.1 and 0.3 micron. After sonication, the liposome suspension was passed through a 1-micron microporous membrane to obtain an aqueous solution of ginsenoside Rg3 blank liposome. Then the aqueous solution was aliquoted into vials and placed in a freeze-dryer for 72 hours. After lyophilization, Then the obtained Rg3 blank liposome was sealed in the vial and protected by argon gas or nitrogen gas. By calculation the D10 diameter of the liposome was 65 nm, D50 was 130 nm, D90 was 143 nm.

Embodiment 10

The Preparation of Paclitaxel Rg3 Liposome

Egg lecithin 0.8 g, ginsenoside 20(S)-Rg3 ultrafine powder 0.2 g and Paclitaxel 0.1 g were mixed with 200 mL chloroform and stirred to form a clear solution at room temperature. The organic solvent was removed by rotary evaporation in a water bath thermostatically controlled at 40° C. to 50° C. to form a film. The formed film was hydrated with 20 mL 5% trehalose aqueous solution (the percentage refers to the ratio of the mass of the trehalose to the total mass of the trehalose aqueous solution) and sonicated until the particle size of the liposome was between 0.1 and 0.3 micron. Thus, an aqueous solution of Paclitaxel Rg3 liposome was obtained. Then the aqueous solution was aliquoted into vials making 30 mg Paclitaxel in each vial. The aqueous solution was placed in a freeze-dryer for 72 hours. After lyophilization, the obtained Paclitaxel Rg3 liposome was sealed in the vial and protected by argon gas or nitrogen gas. By evaluation, the D10 diameter of the liposome was 76 nm, D50 was 90 nm, D90 was 105 nm, the encapsulation efficiency was more than 95%.

Embodiment 11

The Preparation of Paclitaxel Rg5 Liposome

In accordance with the method in embodiment 10, the Paclitaxel Rg5 liposome were prepared by replacing Rg3 with Rg5. By evaluation, the D10 of the liposome was 92 nm, D50 was 128 nm, D90 was 158 nm, the encapsulation efficiency was more than 95%.

Embodiment 12

The Preparation of Paclitaxel Rh2 Liposome

Soybean lecithin 0.7 g, ginsenoside 20(S)-Rh2 ultrafine powder 0.2 g, Paclitaxel 0.1 g, cholesterol 0.1 g, soybean oil 0.1 g and vitamin C 0.1 g were mixed with 200 mL chloroform/acetonitrile (1:1, v/v) and stirred to form a clear solution at room temperature. The organic solvent was removed by rotary evaporation in a water bath thermostatically controlled at 50-60° C. to form a film. The formed film was hydrated with 20 mL 10% treassose aqueous solution (the percentage refers to the ratio of the mass of the trehalose to the total mass of the trehalose aqueous solution) and sonicated until the particle size of the liposome was between 0.1 and 0.3 micron. After sonication, an aqueous solution of paclitaxel Rh2 liposome was obtained. Then the aqueous solution was aliquoted into vials making 30 mg paclitaxel in each vial. The aqueous solution was placed in a freeze-dryer for 72 hours. After lyophilization, the obtained paclitaxel Rh2 liposome was sealed in the vial and protected by argon gas or nitrogen gas. By evaluation, the D10 diameter of the liposome was 79 nm, D50 was 118 nm, D90 was 130 nm, the encapsulation efficiency is more than 95%.

Embodiment 13

The Preparation of Docetaxel Rg3 Liposome

Egg lecithin 0.9 g, ginsenoside 20(S)-Rg3 ultrafine powder 0.18 g, Docetaxel 0.1 g and cholesterol 0.225 g were mixed with 200 mL chloroform/methanol (1:1, v/v) and stirred in a water bath thermostatically controlled at 40-50° C. to form a clear solution. The organic solvent was removed by a membrane evaporator at 50° C. to 60° C. to form a film. The formed film was hydrated with 20 mL 5% sucrose aqueous solution (the percentage refers to the ratio of the mass of the sucrose to the total mass of the sucrose aqueous solution) and homogenized by a high-pressure homogenizer until the particle size of the liposome was between 0.1 and 0.3 micron. After homogenization, the liposome suspension was passed through a 0.22-micron microporous membrane to obtain an aqueous solution of docetaxel Rg3 liposome. Then the aqueous solution was aliquoted into vials making 20 mg docetaxel in each vial. The aqueous solution was placed in a freeze-dryer for 72 hours. After lyophilization, the obtained docetaxel Rg3 liposome was sealed in the vial and protected by argon gas or nitrogen gas. By evaluation, the D10 diameter of the liposome was 70 nm, D50 was 109 nm, D90 was 122 nm, the encapsulation efficiency was more than 95%.

Embodiment 14

The Preparation of Docetaxel Rg5 Liposome

Egg lecithin 0.9 g, ginsenoside Rg5 ultra-fine powder 0.18 g, Docetaxel 0.1 g and cholesterol 0.225 g were mixed with 20 mL chloroform/methanol (1:1, v/v) and stirred in a water bath thermostatically controlled at 40-50° C. to form a clear solution. The organic solvent was removed by a membrane evaporator at 50° C. to 60° C. to form a film. The formed film was hydrated with 20 mL 5% sucrose aqueous solution (the percentage refers to the ratio of the mass of the sucrose to the total mass of the sucrose aqueous solution) and homogenized with a high-pressure homogenizer until the particle size of the liposome was between 0.1 and 0.3 micron. After homogenization, the liposome suspension is filtered by a 0.22-micron microporousmembrane to give an aqueous solution of docetaxel Rg5 liposome. Then the aqueous solution is aliquoted into vials making that each vial contains docetaxel 20 mg, then placed in a freeze-dryer to freeze dry for 72 hours. After lyophilization, the obtained docetaxel Rg5 liposome was sealed in the vial and protected by argon gas or nitrogen gas. By calculation, the D10 of the liposome was 73 nm, D50 was 101 nm, D90 was 118 nm, the encapsulation efficiency was more than 95%.

Embodiment 15

The Preparation of Docetaxel Rh2 Liposome

Soybean lecithin 300 mg, ginsenoside 20(S)-Rh2 ultrafine powder 60 mg, Docetaxel 30 mg, cholesterol 75 mg and mPEG-DSPE 10 mg were mixed with 200 mL chloroform/methanol (1:1, v/v) and stirred to form a clear solution in a water bath thermostatically controlled at 40-50° C. The organic solvent was removed by a membrane evaporator at 50° C. to 60° C. to form a film. The formed film was hydrated with 20 mL 5% sucrose aqueous solution (the percentage refers to the ratio of the mass of the sucrose to the total mass of the sucrose aqueous solution) and homogenized with a high-pressure homogenizer until the particle size of the liposome was between 0.1 and 0.3 micron. After homogenization, the liposome suspension was passed through a 0.22-micron microporous membrane to give an aqueous solution of docetaxel Rh2 liposome. Then the aqueous solution was aliquoted into vials making that each vial contains docetaxel 20 mg, then placed in a freeze-dryer to freeze dry for 72 hours. After lyophilization, the obtained docetaxel Rh2 liposome was sealed in the vial and protected by argon gas or nitrogen gas. By calculation, the D10 diameter of the liposome was 81 nm, D50 was 129 nm, D90 was 148 nm, and the encapsulation efficiency was 95%.

Embodiment 16

The Preparation of Rg3 Irinotecan Liposomes

Egg lecithin 0.9 g, ginsenoside 20(S)-Rg3 ultrafine powder 0.3 g and cholesterol 0.1 g were mixed with 200 mL dichloromethane/ethanol (1:1, V/V) and stirred to form a clear solution at room temperature. The organic solvent was removed by a rotary evaporator in a water bath thermostatically controlled at 50° C. to 60° C. to form a film. The formed film was hydrated with 20 mL 6.6% ammonium sulfate aqueous solution (the percentage refers to the ratio of mass of the ammonium sulfate to the total mass of the ammonium sulfate aqueous solution) and sonicated until the particle size of the blank liposome was between 0.1 and 0.3 micron to give an aqueous solution of Rg3 blank liposome. The solution of the blank liposome was dialyzed against 0.15 mol/L trehalose solution for 12 hours. After dialyzation, a certain amount of trehalose was added according to the volume of the dialyzed blank liposome solution to make the mass percentage of trehalose in the blank liposome solution reach 10% (the mass percentage refers to the mass of the trehalose relative to the total mass of the blank liposome solution). Then, 1 mL irinotecan hydrochloride aqueous solution (containing irinotecan hydrochloride 0.2 g with a mass percentage of 20%) was added and kept for 30 minutes in a water bath at 37° C. to give an aqueous solution of ginsenoside Rg3 irinotecan hydrochloride liposome. The aqueous solution was aliquoted into vials making that each vial contains 40 mg irinotecan hydrochloride, and then placed in a freeze-dryer to freeze dry for 72 hours. The obtained ginsenoside Rg3 irinotecan hydrochloride liposome was sealed in the vial filled with protective gas (argon or nitrogen). By calculation, the D10 diameter of the liposome was 92 nm, D50 was 139 nm, D90 was 165 nm. The encapsulation efficiency was more than 95%.

Embodiment 17

The Preparation of Rg3 Cisplatin Liposome

Egg lecithin 0.8 g, ginsenoside 20(S)-Rg3 ultra-fine powder 0.2 g, cisplatin 0.1 g and soybean oil 0.1 g were mixed with 200 mL chloroform/methanol (1:1, v/v) and stirred to form a clear solution at room temperature. The organic solvent was removed by a rotary evaporator in a water bath thermostatically controlled at 40° C. to 50° C. to form a film. The formed film was hydrated with 20 mL 5% lactose aqueous solution (the percentage refers to the ratio of the mass of the lactose to the total mass of the lactose aqueous solution) and sonicated until the particle size of the liposome was between 0.1 and 0.3 micron. After sonication, the liposome suspension was passed through 1-micron microporous membrane to give an aqueous solution of cisplatin Rg3 liposome. Then the aqueous solution was aliquoted into vials making that each vial contains cisplatin 10 mg, and then placed in a freeze-dryer to freeze dry for 72 hours. After lyophilization, the obtained cisplatin Rg3 liposome was sealed in the vial filled with protective gas (argon or nitrogen). By calculation, the D10 of the liposome was 69 nm, D50 was 109 nm, D90 was 126 nm, and the encapsulation efficiency was more than 95%.

Embodiment 18

The Preparation of Rg3 Doxorubicin Liposome

Soybean lecithin S100 0.9 g, ginsenoside 20(S)-Rg3 ultrafine powder 0.3 g and vitamin E 0.1 g were mixed with 200 mL chloroform/methanol (9:1, v/v) and stirred to form a clear solution in a water bath thermostatically controlled at 40° C.-50° C. The organic solvent was removed by a membrane evaporator at 50° C.-55° C. to form a film. The formed film was hydrated with 20 mL phosphoric acid buffer salt (PBS), stirred to form a clear solution. The clear solution is homogenized by a high-pressure homogenizer until the particle size of the liposome was between 0.1 and 0.3 micron to give an aqueous solution of Rg3 blank liposome. Then the aqueous solution was mixed with 1 mL doxorubicin hydrochloride aqueous solution with a mass percentage of 20% (doxorubicin hydrochloride 0.2 g) and 6 mL disodium hydrogen phosphate aqueous solution with a mass percentage of 7.1%, and purified water was added to adjust pH to 7.30. The mixture was kept in a water bath at 60° C. for 30 minutes to give an aqueous solution of ginsenoside Rg3 doxorubicin hydrochloride liposome. Then the aqueous solution was aliquoted into vials making that each vial contains 20 mg doxorubicin hydrochloride, and placed in a freeze-dryer for 72 hours. After lyophilzation, the obtained ginsenoside Rg3 doxorubicin hydrochloride liposome was sealed in a vial filled with protective gas (argon or nitrogen). By calculation, the D10 diameter of the liposome was 76 nm, D50 was 101 nm, D90 was 125 nm. The encapsulation efficiency was more than 95%.

Application Embodiments

1. Experimental Drugs

Ginsenoside 20(S)-Rg3 (Rg3), paclitaxel, docetaxel, irinotecan hydrochloride, doxorubicin and cisplatin are commercially available in this field.

If without giving specific instructions, the conventional Rg3 liposomes were carried out according to embodiment 1, the Rg3 or Rh2 blank liposomes were carried out according to embodiment 2, Rg5 blank liposomes were carried out according to embodiment 3, Paclitaxel Rg3 liposomes were carried out according to embodiment 10, Paclitaxel Rg5 liposomes were carried out according to embodiment 11, Docetaxel Rg3 liposomes were carried out according to embodiment 13, Docetaxel Rg5 liposomes were carried out according to embodiment 14.

Each ginsenoside blank liposome was either prepared according to the above-mentioned method in the present invention, or according to embodiment 1 and making corresponding changes according to the needs.

2. Instruments

The instruments used in the following embodiments and the application embodiments are self-owned by the School of Pharmacy, Fudan University, and the model and other information of the instruments are listed as follows:

High performance liquid chromatography (HPLC), (Agilent 1100),
Electronic balance (TB-215, Denver Instrument, USA);
Ultrasonic cleaning machine (SB3200DT, Ningbo Xinzhi Biotechnology Co., Ltd.);
Terbovap Sample Concentrator (HGC-12A, Tianjin Hengao Technology Development Co., Ltd.)
Rotary evaporator (RE-2000A, Shanghai Yarong Biochemical Instrument Factory);
Ultrapure water system (ULUP-IV-10T, Sichuan U & P Ultra Technology Co., Ltd.)
Thermostatic oscillator (SHA-C, Changzhou Aohua Instrument Co., Ltd.)
Ultrasonic cell crusher (JY92-II, Ningbo Xinzhi Biotechnology Co., Ltd.);
High pressure homogenizer (EmulsiFlex™-B15, AVESTIN Inc., Canada);
Laser particle size analyzer (Zetasizer Nano ZS, Malvern Panalytical Ltd. UK);
Mini-extruder Equipment (Avanti Polar Lipids Inc);
Photoelectric Microscope (XDS-1B, Chongqing Optical Instrument Co., Ltd.);
Clean bench (SW-CJ-1FD, Suzhou Antai air Technology Co., Ltd.);
Cell incubator (CCL-170B-8, ESCO, Singapore);
Fluorescence inverted microscope (IX-73, Olympus, Japan);
Laser granulometer (Mastersizer 2000, Malvern Panalytical Ltd., UK);
In-vivo Small animal imaging system (In-vivo Multispectral FX PRO, Bruker Corporation, US).

3. Experimental Cell Lines:

4T1 human breast cancer cell line (Nanjing KeyGEN Biotech Co., Ltd)
A549 human lung cancer cell line (Nanjing KeyGEN Biotech Co., Ltd)
BGC-823 human gastric adenocarcinoma cancer cell line (Nanjing KeyGEN Biotech Co., Ltd)
In-situ glioma model in C6 cells (Nanjing KeyGEN Biotech Co., Ltd)
Rat C6 glioma cell line (Nanjing KeyGEN Biotech Co., Ltd)

4. In Vitro Hemolysis Test

Preparation of 2% red blood cell suspension: The blood from a healthy rabbit was collected into a conical flask containing glass beads and shook for 10 minutes, or the blood was agitated using a glass rod to remove the fibrinogen from blood and make defibrinated blood. Then, about 10 times volum of 0.9% sodium chloride solution was added to wash the cell. After centrifugation for 15 minutes at 1000-1500 RPM, the supernatant was discarded and and red blood cells were collected in the precipitation. Then, the red blood cell was obtained after washing the precipitation using 0.9% sodium chloride solution for 2-3 times according to the method above until the supernatant was clear. To obtain a 2% cell suspension, the obtained red blood cells were suspended in 0.9% sodium chloride solution.

Hemolysis Test: 5 clean glass tubes were labelled with numbers. Tube number 1, 2 were used for test samples, tube number 3 was used for negative control, tube number 4 was used for positive control, tube number 5 was used for the contrast sample. As shown in table 5, 2% red blood cell suspension, 0.9% Sodium Chloride Solution, and purified water were added to the tube. After mixing, the tubes were incubated at 37±0.5° C. for 3 h. Results of hemolysis and aggregation were observed and recorded as shown in Table 5.

TABLE 5

| Test tube No. | 1 | 2 | 3 | 4 | 5 |
|---|---|---|---|---|---|
| 2% red cell suspensions/mL | 2.5 | 2.5 | 2.5 | 2.5 | / |
| 0.9% sodium chloride solution/mL | 2.2 | 2.2 | 2.5 | / | 4.7 |
| Purified water/mL | / | / | / | 2.5 | / |
| The test solution/mL | 0.3 | 0.3 | / | / | 0.3 |

If it gave a clear and red solution in the tube, and no cells were settled at the bottom of the tube, it suggested hemolysis occurred. If it gave a colorless or clear solution and red blood cells were all settled at the bottom of the tube, or the supernatant was lightly colored, but no significant differences were observed between tube 1 or 2 and tube 5, it suggested no hemolysis occurred.

If there was red/brown cloudy precipitate in the solution, thoroughly mixed the sample by gently inverting the tube 3 times. If the precipitate was still there, it indicated red blood cell aggregation. The sample should be further observed under microscope to confirm if red blood cell aggregation occurred.

Results Analysis: If no hemolysis or aggregation occurs in the tube of negative control, but hemolysis occurred in the tube of positive control, and no hemolysis and aggregation occurs in the two tubes of test samples within 3 hours, the test sample meet the regulations. If hemolysis and aggregation occurs in one of the tubes with test sample within 3 hours, four more sample tests should be performed to confirm. Only when no hemolysis and aggregation occurs within 3 hours in all the four sample tubes, the test sample can be conformed that it meets the requirements, otherwise the test sample does not meet the requirements.

In a specific experiment, concentration of the test sample (ginsenoside) can be adjusted according to the needs.

5. Experimental Animals

Experimental animals: Kunming mice (or normal mice) are purchased from the Animal Center of the Third Military Medical University, BALB/C-nu/nu mice (or nude mice) are purchased from Shanghai SlACK Laboratory Animal Co., Ltd.

6. Cell Culture Method

Cell lines were incubated at 37° C. in a humidified incubator with 5% $CO_2$, and cultured in DMEM or RPMI1640 complete culture-medium supplemented with 10% fetal bovine serum, 100 U/mL penicillin and 100 µg/mL streptomycin. A solution of 0.25 trypsin-EDTA was used for sub-culturing cells, which was performed 2 to 3 times per week.

7. Drug Administration

A negative control group (e.g. PBS group), a positive control group and a sample group (ginsenoside liposome loaded with a drug) were set up for each experiment. A total of 3-6 concentration gradients were set up, including half dilution or 5 times dilution. Each concentration repeated 3 times.

8. Determination of the Half-Maximal Inhibitory Concentration ($IC_{50}$) of Tumor Cell Tumor cells in logarithmic growth phase were digested with trypsin and centrifuged, collected the cell pellet and resuspended it in a buffer. Then cells in the suspension solution were counted and seeded into a 96-well culture plate with 5000 cells per well by placing 100 µl cell suspension solution in each well. On the next day, 100 µl fresh culture medium containing different concentrations of samples or solvent as control were added to each well respectively (with a final concentration of DMSO<0.5%). For each sample, 10 different dose groups were set up, and each group repeated 3 times parallelly. After 72-hour incubation at 37° C., the supernatant was discarded and 100 µl PBS and 10 µl CCK-8 were added to each well. Then the plate was well shaked using a micro oscillator for uniform and continually cultured for 3 h. Absorbance is determined by a microplate reader at a reference wavelength of 630 nm and a detection wavelength of 450 nm. Tumor cells treated with a solvent were used as a control, $IC_{50}$ is computed from the median-effect equation.

9. Determination of Cell Viability In Vitro

Logarithmically growing tumor cells were collected and resuspended in DMEM complete medium supplemented with 10% fetal bovine serum, 100 U/ml penicillin and 100 µg/ml streptomycin to a final cell density of $4\times10^4$ cells/ml. Then, 200 µl cell suspension solution was seeded into each well of a 96-well plate (with a concentration of $8\times10^3$ cells/well) and the plate was cultured in a $CO_2$ cell culture incubator at 37° C. After 48 h, DMEM complete medium was removed and respectively replaced with 200 µL different concentrations of anti-cancer drug, at least 6 different concentration groups. The group without replacing DMEM complete medium by anti-cancer drug solution was used as negative control. For each concentration group, 4 replicates were set up. The whole experiment was independently repeated 3 times. The cells were continuously cultured in a $CO_2$ cell culture incubator at 37° C. After 72 h, 20 µl 5 mg/mL MTT solution was added into each well and the plate was continuously cultured for 4 h. Then discarded the supernatant, added 150 µl DMSO into each well, and shaked the plate for 10 min. The absorbance was measured at 490 nm using a microplate reader (Tecan infinite M 200 TECAN, Switzerland). The cell survival rate is calculated according to the following formula:

$$\text{Cell Survival Rate (\%)} = \frac{Abs_{490(sample)}}{Abs_{490(control)}} \times 100$$

Wherein $Abs_{490(sample)}$ is the absorbance of the experimental sample, $Abs_{490(control)}$ is the absorbance of the negative control.

Small Animal Imaging In Vivo

As shown in the embodiments.

11. In-Vivo Drug efficacy Test 100 uL logarithmically growing tumor cells with a density of $1\times10^7$ to $10\times10^7$ cells/mL was injected subcutaneously into the right armpit of an 18 to 20 g nude mouse slowly using a 1 mL syringe. The growth of the tumor was observed. When the tumor volume was about 100 mm$^3$, animals were randomized to groups and administered with different drugs. All mice were weighed, and the longest diameter and the shortest diameter of the tumor was measured with vernier calipers every two days. At the end of the experiment, the nude mice were sacrificed and the volumes of tumors were calculated. Then, the relative tumor volume (RTV), T/C ratio (the ratio of tumor volume in control versus treated mice) and the percent tumor growth inhibition (TGI) were calculated and statistically analyzed.

Tumor volume was calculated according to the following formula: $V=(L\times W\times H)/2$, wherein V is tumor volume, L is tumor length, W is tumor width, H is tumor height.

Relative tumor volume was calculated according to the following formula: $RTV=TV_n/TV_0$, wherein $TV_n$ is the tumor volume at day n, $TV_0$ is the tumor volume at day zero (the administration day).

The T/C ratio was determined by calculating RTV: T/C (%)=TRTV/CRTV×100%, wherein TRTV is the RTV of the treatment group, CRTV is the RTV of the control group.

The percent tumor growth inhibition (TGI) was calculated according to the following formula:

TGI(%)=((MTVcontrol−MTVtreated/MTVcontrol))× 100, wherein MTVcontrol is the median tumor volume of control group, MTVtreated is the median tumor volume of the drug treatment group.

Curative effect was evaluated based on the T/C ratio: T/C (%)>60 means the treatment has no effect; T/C (%)≤60 and the differences between the treatment group and the control group are statistically significant (P<0.05) means the treatment is effective.

In the following application embodiments, C(µM) means concentration, wherein the concentration of Taxol+Rg3 refers to the concentration of paclitaxel and ginsenoside Rg3 in the ginsenoside Rg3 paclitaxel liposome, for example, 5+30 means that in ginsenoside Rg3 paclitaxel liposome, the concentration of the paclitaxel is 5 µM and the concentration of the ginsenoside Rg3 is 30 µM. Time (d) is calculated by days.

12. Analysis Method of Paclitaxel

Analysis of paclitaxel is according to the Paclitaxel analysis method in the United States Pharmacopeia (USP 34).

Application Embodiments

Embodiment 1

Hemolysis Test

Experimental results are listed in table 1. HD50 is 50% of the maximum haemolysis.

TABLE 1

| Embodiment No. | Abbreviation of Liposome Name | Liposome Full Name | Hemolysis (HD50) |
| --- | --- | --- | --- |
| Embodiment 1 | Rg3-Cho-Lipo | conventional Rg3 cholesterol liposome | 20-50 μg/mL |
| Embodiment 2 | Rg3-blank | Rg3 blank liposome | 650-700 μg/mL |
| Embodiment 3 | Rg5-blank | Rg5 blank liposome | 450-500 μg/mL |
| Embodiment 7 | Rh2-blank | Rh2 blank liposome | 400-500 μg/mL |
| Embodiment 10 | PTX-Rg3-Gipo | Paclitaxel Rg3 Liposome | 650-700 μg/mL |
| Embodiment 11 | PTX-Rg5-Gipo | Paclitaxel Rg5 Liposome | 450-500 μg/mL |
| Embodiment 12 | PTX-Rh2-Gipo | Paclitaxel Rh2 Liposome | 400-500 μg/mL |
| Embodiment 13 | DTX-Rg3-Gipo | Docetaxel Rg3 Liposome | 650-700 μg/mL |
| Embodiment 14 | DTX-Rg5-Gipo | Docetaxell Rg5 Liposome | 450-500 μg/mL |
| Embodiment 15 | DTX-Rh2-Gipo | Docetaxel Rh2 Liposome | 400-500 μg/mL |

As shown in Table 1, Rg3-Cho-Lipo showed severe hemolytic effect, whereas the hemolytic effects of Rg3-Blank, Rh2-Blank, PTX-Rg3-Gipo, PTX-Rh2-Gipo, DTX-Rg3-Gipo and DTX-Rh2-Gipo were similar to those of Rg5-Blank, PTX-Rg5-Gipo and DTX-Rg5-Gipo with HD50 value in the range of 400-700 μg/mL, which can meet the safety standards of medicinal products.

In addition, conventional Rg3-Cho-Lipo did not show hemolysis up to a concentration of 20-50 μg/mL, mainly because that the encapsulation efficiency of the conventional Rg3 cholesterol liposome was low and Rg3 may leak more or less, thereby affecting the drug efficacy. Whereas, the encapsulation efficiency of the ginsenoside liposomes obtained from embodiment 2, embodiment 3, embodiment 7, embodiment 10, embodiment 12-13 and embodiment 15 in the present invention were high, similar to the encapsulation efficiency of Rg5-blank, PTX-Rg5-Gipo and DTX-Rg5-Gipo, thus, these drugs were all very efficient. Besides Rg3 and Rh2, it can further encapsulate drugs, such as Paclitaxel, indicating that Rg3 is used as membrane material in these liposomes.

Application Embodiment 2

Studies on the Effect of Mass Percentage of Ginsenoside in the Liposome on the Average Particle Size of the Liposome Sample test before lyophilization: 20 mL sample solution was diluted into 900 mL purified water at room temperature. The mixture was stirred for 1 min at 1700 rpm/min. Then, the sample was tested and the results were recorderd.

Sample test after lyophilization: A vial of lyophilized sample was hydrated with 20 mL purified water. Then, shaked the vial until the sample was fully dissolved. The sample solution was diluted into 900 mL purified water at room temperature and stirred for 1 min at 1700 rpm/min. Then, the sample was tested and the results were recorded. The experimental results are shown in Table 2.

TABLE 2

Effects of mass percentage of ginsenoside in the liposome on the average particle size of the liposome

| Name | Preparation method | Mass percentage of 20(S)-Rg3 in liposomes | Average particle size | Encapsulation efficiency |
| --- | --- | --- | --- | --- |
| Rg3-cholesterol liposome | According to embodiment 1 | Egg lecithin:Rg3 = 10:0.1 | 147 nm | ≥95% |
| | | Egg lecithin:Rg3 = 10:1 | 438 nm | ≥85% |
| | | Egg lecithin:Rg3 = 10:2 | ≥1 μm | ≤80% |
| | | Egg lecithin:Rg3 = 10:5 | ≥1 μm | ≤80% |
| Rg3-Blank liposome | ccording to embodiment 2 | Egg lecithin:Rg3 = 10:0.1 | 116 nm | ≥95% |
| | | Egg lecithin:Rg3 = 10:1 | 92 nm | ≥95% |
| | | Egg lecithin:Rg3 = 10:2 | 126 nm | ≥95% |
| | | Egg lecithin:Rg3 = 10:5 | 185 nm | ≥95% |
| Paclitaxel-Rg3 Liposome | According to embodiment 10 | Egg lecithin:Rg3:Paclitaxel = 10:0.1:0.05 | 103 nm | ≥95% |
| | | Egg lecithin:Rg3:paclitaxel = 10:1:0.5 | 85 nm | ≥95% |
| | | Egg lecithin:Rg3:Paclitaxel = 10:2:1 | 157 nm | ≥95% |
| | | Egg lecithin:Rg3:paclitaxel = 10:5:2.5 | 243 nm | ≥95% |

As showed in Table 2, the particle size increased and encapsulation efficiency decreased while increasing the mass percentage of Rg3 in Rg3-cholesterol liposome. Huan Yu, et al disclosed a Rg3-cholesterol liposome, which, in fact, is a conventional blank liposome loaded with Rg3 (See: International Journal of Pharmaceutics 450(2013)250-258). In the conventional Rg3-cholesterol liposomes, Rg3 is an active substance. With the increasing mass percentage of the Rg3, the encapsulation efficiency decreases and the particle size increases. Whereas, in the present invention, Rg3 is used as membrane material. With the increasing mass percentage of Rg3, particle size of the liposome becomes smaller and all the encapsulation efficiency are more than 95%. Therefore, Rg3 is used as membrane material in the present invention. Properties of the liposome also changes with the changes of the membrane material.

Application Embodiment 3

The Determination of Particle Size Distribution, Dispersion Coefficient and Electron Microscope Imaging of Paclitaxel Cholesterol Liposome and Paclitaxel Rg3 Liposome The determination of particle size distribution and dispersion coefficient: samples of PTX-Cho-Lipo and PTX-Rg3-Gipo were diluted 10 times. Then 1 mL diluted solution was added into the sample pool of Malvern laser particle size analyzer. Test results were recorded and analyzed.

Morphology test of liposomes: 150 μL PTX-Cho-Lipo solution and PTX-Rg3-Gipo solution were each diluted into 5 mL purified water. After dilution, a drop was placed on a carbon-coated copper grid and air dried for 10 minutes, then the sample was stained with 2% sodium acetate for 30 minutes. After removing the excess staining solution using a filter paper, the morphology of liposomes was observed and imaged using transmission electron microscope (TEM).

The experimental results are listed in Table 3.

TABLE 3

The particle sizes of PTX-Cho-Lipo and PTX-Rg3-Gipo

| Name | Mean Particle size ±SD (nm) | Distribution coefficient (PDI) | Zeta Potential |
|---|---|---|---|
| Paclitaxel cholesterol liposome (PTX-Cho-Lipo) | 114.4 ± 5.18 | 0.27 ± 0.004 | −8.7 ± 2.128 |
| Paclitaxel Rg3 liposome (PTX-Rg3-Gipo) | 77.8 ± 6.41 | 0.17 ± 0.015 | −4.2 ± 0.777 |

Figure 2:
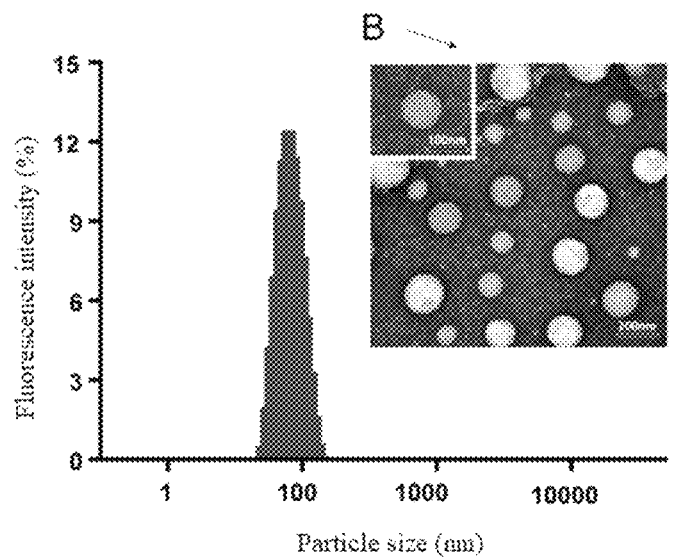
FIG. 2 is the particle size distribution of the paclitaxel-loaded liposome with Rg3 as membrane material, wherein B is the electron microscopy image showing the particle size of the liposome loaded with paclitaxel and cholesterol.

As shown in FIGS. 1 and 2, FIG. 2 represents a normal distribution. As shown in Table 3, the distribution coefficient of PTX-Rg3-Gipo in the present invention is more optimal than that of PTX-Cho-Lipo, and the particle size of PTX-Rg3-Gipo is also smaller. The results suggest that PTX-Rg3-Gipo is better than PTX-Cho-Lipo in quality.

Application Embodiment 4

The Leakage Experiment of PTX-Cho-Lipo and PTX-Rg3-Gipo

Freshly prepared PTX-Cho-Lipo and PTX-Rg3-Gipo were filtered using 0.22 micron membrane, and their encapsulation efficiency was determined and considered as a 100%. 3 mL each of the PTX-Cho-Lipo and PTX-Rg3-Gipo solutions were taken out and stored at 4° C. and their encapsulation efficiency were measured daily for 7 days. Plot a graph between the encapsulation efficiency and the time (days).

Figure 3:
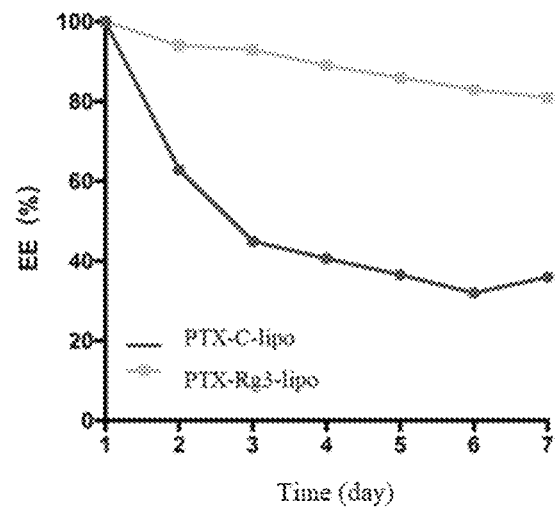
FIG. 3 is the results of leakage of Paclitaxel in Paclitaxel cholesterol-liposome (PTX-Cho-Lipo) and Paclitaxel Rg3-liposome (PTX-Rg3-Gipo).

The experimental results are shown in FIG. 3 and table 4.

TABLE 4

The encapsulation efficency of paclitaxel in PTX-Cho-Lipo and PTX-Rg3-Gipo

| | Encapsulation efficiency, % | |
|---|---|---|
| Time(days) | PTX-Cho-Lipo | PTX-Rg3-Gipo |
| 1.00 | 100.00 | 100.00 |
| 2.00 | 62.90 | 94.32 |
| 3.00 | 44.95 | 89.67 |

TABLE 4-continued

The encapsulation efficency of paclitaxel in PTX-Cho-Lipo and PTX-Rg3-Gipo

| | Encapsulation efficiency, % | |
|---|---|---|
| Time(days) | PTX-Cho-Lipo | PTX-Rg3-Gipo |
| 4.00 | 40.61 | 85.85 |
| 5.00 | 36.57 | 83.37 |
| 6.00 | 33.25 | 81.68 |
| 7.00 | 35.85 | 80.32 |

As shown in FIG. 3, there is a sharp drop in the encapsulation efficiency of PTX-Cho-Lipo from the beginning to the third day, however, few changes are observed in the encapsulation efficiency of PTX-Rg3-Gipo within 7 days.

As shown in Table 4, under the same conditions, encapsulation efficiency of PTX-Rg3-Gipo in the present invention is higher than that of PTX-Cho-Lipo, which indicates that PTX-Rg3-Gipo is more stable in solution with less leakage. Thus, the quality of PTX-Rg3-Gipo is better than PTX-Cho-Lipo, and Rg3 is better than cholesterol as a liposome membrane material.

Application Embodiment 5

Effects of Liposome on Prolonged Circulation Time 30 nude mice (18-22 g) were randomly divided into 5 various groups (6 in each group), administered via mouse tail vein respectively with 0.3 mg/kg Cholesterol-blank liposome loaded with a fluorescent dye DID (DID-Cho-blank), mPEG-DSPE-Cholesterol blank liposome loaded with a fluorescent dye DID (DID-PEG-blank), Rg5-blank liposome loaded with loaded with a fluorescent dye DID (DID-Rg5-blank), Rg3-blank liposome loaded with a fluorescent dye DID (DID-Rg3-blank) and Rh2-blank liposome loaded with a fluorescent dye DID (DID-Rh2-blank). 0.2 mL blood samples were collected into heparinized centrifugal tubes via mice facial vein respectively after 2 min, 5 min, 15 min, 30 min, 1 hour, 3 hour, 6 hour, 12 hour and 24 hour. The DID fluorescence intensity of the collected blood sample was measured by a microplate reader. The fluorescence intensity of the first sample collected after 2 min was considered as 100% and other fluorescence intensity were calculated based on this value.

Data Process and Analysis: The pharmacokinetic parameters of each liposome were calculated using pharmaceutical kinetics software 3p97, including Area under the Concentration-time Curve (AUC), half life of distribution ($t_{1/2\alpha}$, $t_{1/2\beta}$) and half-life of elimination($t_{1/2\gamma}$), etc.

Figure 4:
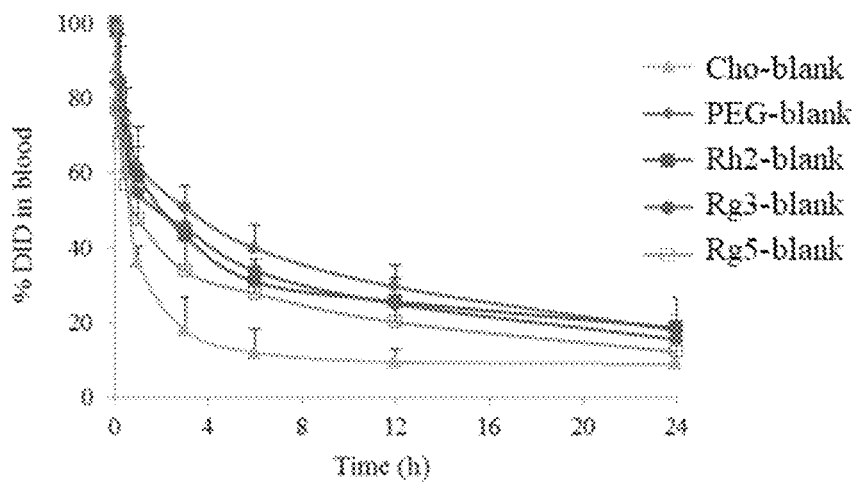
FIG. 4 is the long-circulation effects of the blank cholesterol-liposome (Cho-Blank), blank mPEG-DSPE-Cholesterol-Liposome (PEG-Blank), blank Rg5-Liposome (Rg5-blank), blank Rg3-Liposome (Rg3-blank) and blank Rh2-Liposome (Rh2-blank).

The experimental results are listed in FIG. 4 and Table 5.

TABLE 5

Characterization of liposome on prolonged ciruculation time

| Parameter | DID-Cho-blank | DID-PEG-blank | DID-Rg5-blank | DID-Rg3-blank | DID-Rh2-blank |
|---|---|---|---|---|---|
| $t_{1/2\alpha}$/h | 0.03 | 0.016 | 0.017 | 0.67 | 0.245 |
| $t_{1/2\beta}$/h | 0.798 | 0.917 | 0.47 | 1.603 | 1.892 |
| $t_{1/2\gamma}$/h | 9.049 | 24.647 | 12.999 | 27.243 | 24.844 |
| AUC(0-t)/mg · L · h | 401.352 | 808.472 | 450.461 | 753.111 | 760.584 |
| AUC(0-∞)/mg · L · h | 455.227 | 1163.13 | 613.035 | 827.905 | 916.252 |

As shown in Table 5, the values of AUC, half life of distribution (t1/2α, t1/2β) and half-life of elimination (t1/2γ) of DID-Rg3-blank and DID-Rh2-blank liposomes in the present invention are similar to the values of DID-PEG-blank, suggesting that they all have similar prolonged circulation time and similar therapeutic effect. Whereas, the circulation time and therapeutic effects of DID-Rg5-blank is shorter and weaker than DID-PEG-blank, only longer and stronger than the conventional DID-Cho-Blank.

Application Enbodiment 6

In Vivo Target Specificity Assay

BALB/C-nu/nu mice bearing tumors in uniform size of 100 mm³ at right forelimbs without hemorrhagic necrosis, were intravenously injected via tail vein with liposomes in the present invention carrying 10% of near-infrared fluorescent probe (IR783) respectively (hereinafter named as the experimental group), which was obtained by encapsulating near-infrared fluorescent probe (IR783) into the present ginsenoside blank liposome, see embodiment 10 for details. A conventional blank lipsome caning near-infrared fluorescent probe (IR783) was hereinafter named as the control group which was obtained by encapsulating near-infrared fluorescent probe (IR783) into the blank liposome. The in vivo distributions of IR783 fluorescence were were recorded by in-vivo animal imaging system at the following time points, 2 h, 4 h, 8 h, 12 h and 24 h hour after administration, see FIG. 5.

Figure 5:
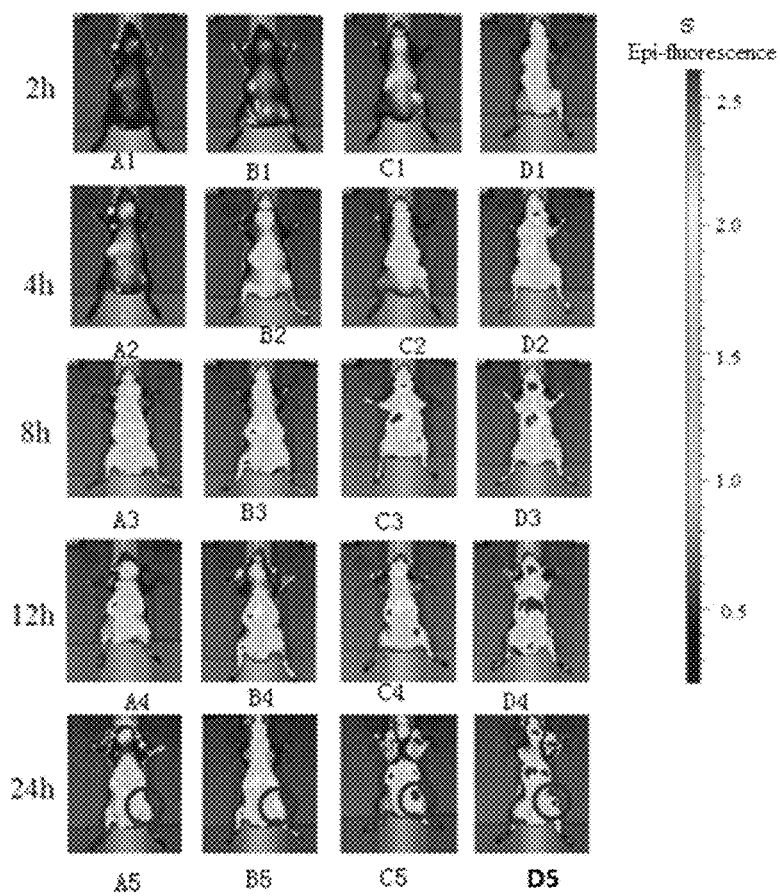
FIG. 5 is in vivo IR783 fluorescence distribution of Control group(IR783-Cho-Lipo), IR783-Rg5-Gipo group, IR783-Rg3-Gipo group and IR783-Rh2-Gipo group at the $2^{nd}$, $4^{th}$, $8^{th}$, $12^{th}$ and $24^{th}$ hour after administration; wherein, FIGS. 5-A1-A5 are respectively the fluorescence distribution of the Control group at the $2^{nd}$, $4^{th}$, $8^{th}$, $12^{th}$ and $24^{th}$ hour.

FIG. 5-A1-A5 are respectively in vivo distribution of IR783 fluorescence in the control group recorded at $2^{nd}$, $4^{th}$, $8^{th}$, $12^{th}$ and $24^{th}$ hour by in-vivo animal imaging system. FIG. 5-S is a fluorescence ruler, wherein the color is red, yellow, green and blue in sequence, indicating the fluorescence intensity, from the strongest to the weakest. FIG. 5-B1-B5, FIG. 5-C1-C5 and FIG. 5-D1-D5 are respectively the in vivo fluorescence distribution in the experimental group recorded at $2^{nd}$, $4^{th}$, $8^{th}$, $12^{th}$ and $24^{th}$ hour by in-vivo animal imaging system. FIG. 5-B1-B5 are respectively the fluorescence distribution of the Rg5-blank group; FIG. 5-C1-C5 are respectively the fluorescence distribution of the Rh2-blank group; FIG. 5-D1-D5 are respectively the fluorescence distribution of the Rg3-blank group.

As shown in FIG. 5, the right forelimbs of the mice in the control group had no fluorescence, while the right forelimbs of the mice in the experimental groups have intensive fluorescence, indicating that ginsenoside blank liposomes can target tumor cells specifically.

Figure 6:
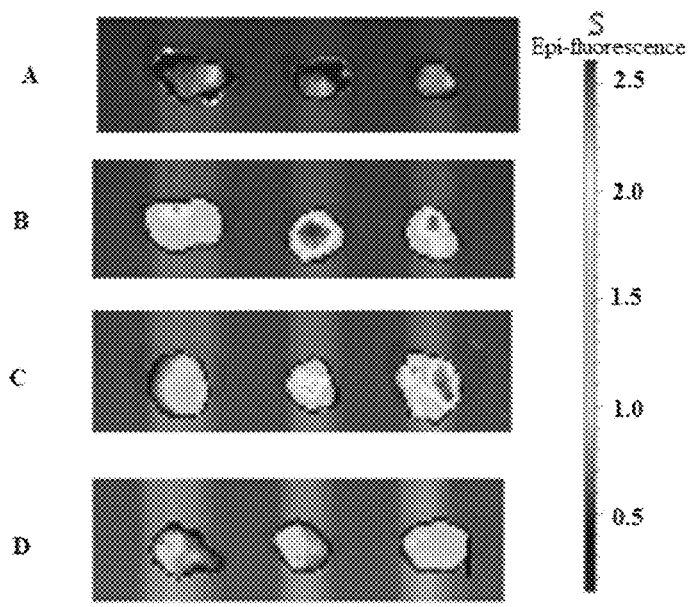
FIG. 6 is the in vivo IR783 fluorescence distribution that recorded at $24^{th}$ hour.

FIG. 6 is the in-vitro fluorescence distribution of IR783 after tumor removal imaged by in-vivo animal imaging system. FIG. 6-A is control group, and FIGS. 6-B, 6-C and 6-D are the experimental groups. After the in-vivo imaging, the tumors in the experimental group and control group are taken out and imaged in vitro. FIG. 6-S is a fluorescence ruler, wherein the color shows the relative fluorescence intensity, from strongest to weakest in a sequence of red, yellow, green and blue. FIG. 6-B, FIG. 6-C and FIG. 6-D respectively show the fluorescence intensity of Rg5-Gipo, Rg3-Gipo and Rh2-Gipo groups, suggesting that ginsenoside blank liposomes have very high specificity toward tumor cells.

Figure 7:
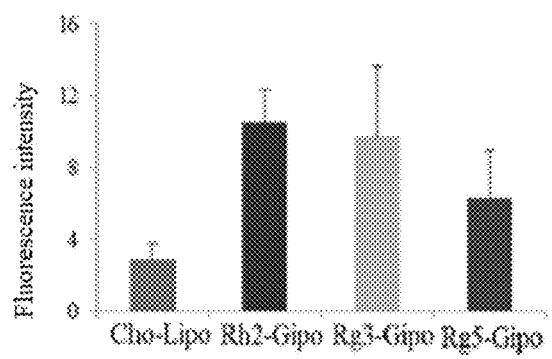
FIG. 7 is the statistical analysis of fluorescence intensity in tumor-bearing mice of Control group, IR-783-Rh2-Gipo group, IR-783-Rg3-Gipo group and IR-783-Rg5-Gipo group.

FIG. 7 is the comparison results between the fluorescence intensity of the control group and the experimental groups. It shows that the fluorescence intensity of Rg5-Gipo, Rg3-Gipo and Rh2-Gipo are significantly higher than that of the control group. Rg3-Gipo and Rh2-Gipo exhibit a significantly higher specificity to target than Rg5-Gipo group in BGC-823 human gastric cancer.

In summary, the results suggest that Rg5-blank, Rg3-blank, and Rh2-blank have significantly higher specificity to target than the Cho-blank liposome. Moreover, Rg3-blank and Rh2-blank show a higher targeting specificity than Rg5-blank.

Application Embodiment 7

In Vivo and In Vitro Pharmacological Efficacy Assay

1. In Vitro Drug Efficacy Assay

Figure 8:
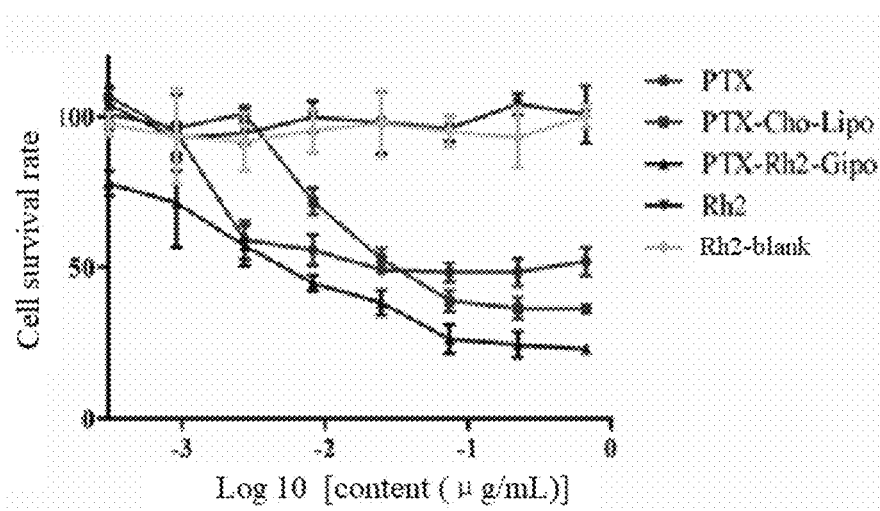
FIG. 8 is the cell survival rate of human breast cancer cell line (4T1) with addition of Rh2 group, Rh2-blank group, PTX group, PTX-Cho-Lipo group, PTX-Rh2-Gipo group

To test the drug efficacy in vitro, a total of 8 various concentrations were set up as shown in Table 6 and FIG. 8. FIG. 8 shows the cell survival rate of human breast cancer cell line (4T1) with addition of Rh2 group, Rh2-blank group, PTX group, PTX-Cho-Lipo group and PTX-Rh2-Gipo group respectively.

TABLE 6

Concentration and viability of human breast cancer cells (4T1) with addition of Rh2 group, Rh2-blank group, PTX group, PTX-Cho-lipo group and PTX-Rh2-Gipo group

| C(μM) | | | | | Cell Viability | | | | |
|---|---|---|---|---|---|---|---|---|---|
| Rh2 | Rh2-blank | PTX | PTX-Cho-Lipo | PTX-Rh2-Gipo | Rh2 | Rh2-blank | PTX | PTX-Cho-Lipo | PTX-Rh2-Gipo |
| 8.00000 | 8.00000 | 2.00000 | 2.00000 | 2.00000 | 100.73 | 100.25 | 52.00 | 36.52 | 23.07 |
| 2.66667 | 2.66667 | 0.66667 | 0.66667 | 0.66667 | 104.25 | 93.08 | 48.54 | 36.50 | 24.47 |
| 0.88889 | 0.88889 | 0.22222 | 0.22222 | 0.22222 | 96.04 | 95.03 | 48.48 | 39.00 | 26.36 |
| 0.29630 | 0.29630 | 0.07407 | 0.07407 | 0.07407 | 98.07 | 97.72 | 49.25 | 52.92 | 38.40 |
| 0.09877 | 0.09877 | 0.02469 | 0.02469 | 0.02469 | 99.90 | 95.43 | 55.83 | 71.95 | 44.87 |
| 0.03292 | 0.03292 | 0.00823 | 0.00823 | 0.00823 | 94.47 | 91.77 | 59.19 | 101.07 | 57.24 |
| 0.01097 | 0.01097 | 0.00274 | 0.00274 | 0.00274 | 92.85 | 93.55 | 94.70 | 96.12 | 71.48 |
| 0.00366 | 0.00366 | 0.00091 | 0.00091 | 0.00091 | 104.04 | 97.43 | 106.72 | 101.03 | 77.96 |

As shown in Table 6 and FIG. 8, free Rh2 and Rh2-blank groups show low activity in vitro against human breast cancer cells (4T1). With low concentration, the cell viability of PTX-Cho-lipo group is lower than PTX group. While no matter the concentration is high or low, the cell viability of PTX-Rh2-Gipo group is much higher than the PTX group.

2. In Vivo Drug Efficacy Assay

To evaluate the drug efficacy in vivo, 45 subcutaneous tumor-bearing nude mice were randomized into 5 treatment groups (9 in each group) and intravenously injected with PBS solution (control group), ginsenoside Rh2 (Rh2 group), ginsenoside Rh2 blank liposome (Rh2-Blank group), conventional paclitaxel cholesterol liposome (PTX-Cho-Lipo group) and ginsenoside Rh2 paclitaxel liposome (PTX-Rh2-Gipo group) via tail vein at a dose of 30 mg/kg. The changes of body weights of mice in each group were recorded every 2 days, and the longest diameter and the shortest diameter of tumors were measured with vernier calipers. The tumor volume was calculated by the following formula: $V=(dmax \times dmin^2)/2$, wherein dmin and dmax are respectively the shortest diameter and the longest diameter (mm) of the tumor; a relative tumor volume (RTV) was calculated according to the measurement results, by the formula: $RTV=TVn/TV_0$, wherein TVn is the volume of the tumor measured every 2 days, $TV_0$ is the volume of the tumor measured at day zero (the administration day).

TABLE 7

Antitumor effects of control group, Rh2 group, Rh2-blank group, PTX-Cho-lipo group and PTX-Rh2-Gipo group in human breast cancer cell 4T1

| 4T1 time(d) | Relative tumor volume | | | | |
|---|---|---|---|---|---|
| | Control | Rh2 | Rh2-blank | PTX-Cho-Lipo | PTX-Rh2-Gipo |
| 0 | 100.00 | 100.00 | 100.00 | 100.00 | 100.00 |
| 3 | 273.99 | 200.94 | 214.73 | 199.01 | 95.23 |
| 6 | 249.60 | 316.69 | 193.95 | 229.01 | 166.89 |
| 9 | 290.21 | 276.04 | 273.64 | 289.80 | 162.85 |
| 12 | 555.41 | 400.20 | 310.41 | 317.20 | 168.02 |
| 15 | 507.64 | 473.53 | 403.28 | 435.89 | 167.88 |
| 18 | 700.78 | 510.20 | 400.30 | 449.06 | 178.55 |
| 21 | 965.30 | 898.52 | 603.59 | 511.90 | 245.27 |

Figure 9:
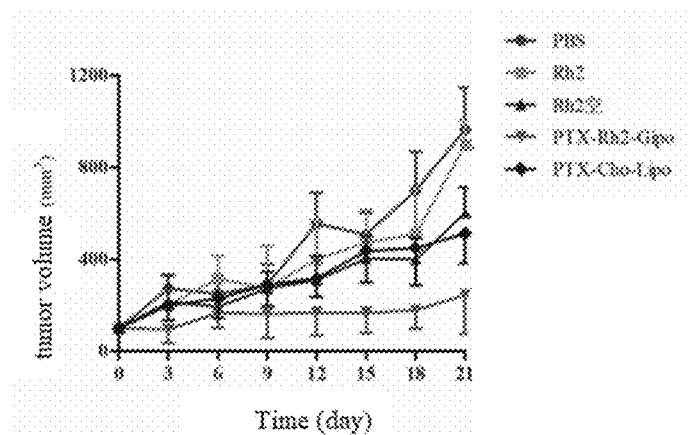
FIG. 9 is the relative tumor volume of Control group, Rh2 group, Rh2-blank group, PTX-Cho-Lipo group, PTX-Rh2-Gipo group in human breast cancer cell line (4T1).

As shown in Table 7 and FIG. 9, after the same period of time, the volume of tumor in control group and Rh2 group are the maximum while in the PTX-Rh2-Gipo group is the minimum, followed by PTX-Cho-lipo group and Rh2-blank group. Results suggest that PTX-Rh2-Gipo group has better antitumor effects.

3. In Vitro Cytotoxicity Studies

The in vitro cytotoxicity was evaluated using human breast cancer cell line (4T1). The cell survival rate of human breast cancer cell line (4T1) with addition of DTX group, DTX-Cho-Lipo group, DTX-Rg3-Gipo group and Nanoxel-PM group at various concentration were shown in Table 8 and FIG. 10.

TABLE 8

The viability of human breast cancer cells (4T1) with addition of DTX group, DTX-Cho-Lipo group, DTX-Rg3-Gipo group and Nanoxel-PM group at various concentration

| Concentration (µg/ml) | Cell viability(%) | | | |
|---|---|---|---|---|
| | DTX | DTX-Cho-Lipo | DTX-Rg3-Gipo | Nanoxel-PM |
| 3 | 51.85 | 39.85 | 40.67 | 40.54 |
| 0.6 | 48.89 | 40.96 | 43.98 | 44.78 |
| 0.12 | 46.26 | 45.56 | 42.60 | 37.62 |
| 0.024 | 49.86 | 55.45 | 48.52 | 44.52 |
| 0.0048 | 50.94 | 54.08 | 48.94 | 51.03 |
| 0.00096 | 61.65 | 59.35 | 50.33 | 61.96 |
| 0.00019 | 72.48 | 69.81 | 52.11 | 76.16 |
| 3.84E−05 | 83.55 | 76.62 | 65.00 | 84.21 |
| 7.68E−06 | 86.66 | 79.15 | 81.59 | 88.55 |

Figure 10:
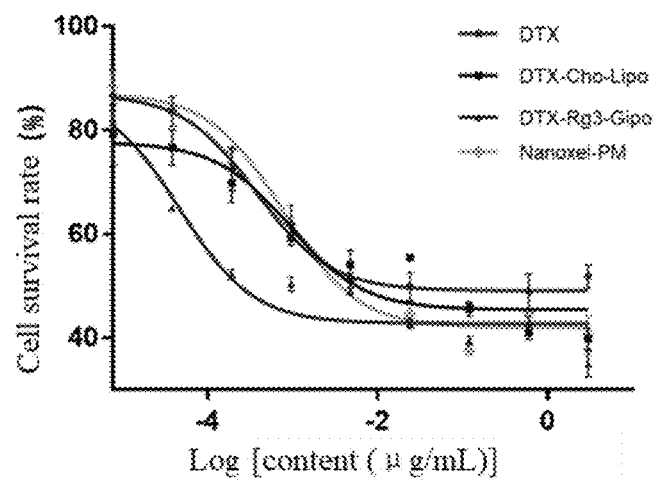
FIG. 10 is the cell survival rate of human breast cancer cell line (4T1) with addition of DTX group, DTX-Cho-Lipo group, DTX-Rg3-Gipo group

As shown in Table 8 and FIG. 10, after the same period of time, the overall viability of human breast cancer cells 4T1 with addition of DTX-Rg3-Gipo group is significantly higher than DTX-Cho-Lipo group, especially in lower concentrations.

4. In Vivo Drug Efficacy Assay

To evaluate the drug efficacy in vivo, 45 subcutaneous tumor-bearing nude mice were were randomized into 5 groups (9 in each group), and intravenously injected with PBS solution (Control group,), Taxotere, Nanoxel-PM, DTX-Rg5-Gipo and DTX-Rg3-Gipovia tail vein at a dose of 10 mg·kg$^{-1}$. The changes in mice body weights in each group were recorded every 2 days, and the longest diameter and the shortest diameter of tumors were measured with vernier calipers. The tumor volume is calculated by the following formula: $V=(dmax \times dmin^2)/2$, wherein dmin and dmax are respectively the shortest diameter and the longest diameter (mm) of the tumor; a relative tumor volume (RTV) is calculated according to the measurement results by the formula: $RTV=TVn/TV_0$, wherein TVn is the volume of the tumor measured every 2 days, $TV_0$ is the volume of the tumor measured at day zero (the administration day).

TABLE 9

Antitumor effect of Control group, Taxotere group, Nanoxel-PM group, DTX-Rg5-Gipo group and DTX-Rg3-Gipo group in human breast cancer cell 4T1

| 4T1 time(d) | Relative tumor volume | | | | |
|---|---|---|---|---|---|
| | Control | Taxotere | Nanoxel-PM | DTX-Rg5-Gipo | DTX-Rg3-Gipo |
| 0 | 100.00 | 100.00 | 100.00 | 100.00 | 100.00 |
| 3 | 273.99 | 206.85 | 192.51 | 168.40 | 115.34 |
| 6 | 249.60 | 254.61 | 140.99 | 141.67 | 84.92 |
| 9 | 290.21 | 198.66 | 172.59 | 203.55 | 125.33 |
| 12 | 555.41 | 224.67 | 134.94 | 155.11 | 89.09 |
| 15 | 507.64 | 231.03 | 181.05 | 150.37 | 86.65 |
| 18 | 700.78 | 361.50 | 175.55 | 197.97 | 65.99 |
| 21 | 764.79 | 322.15 | 184.46 | 151.56 | 86.11 |

Figure 11:
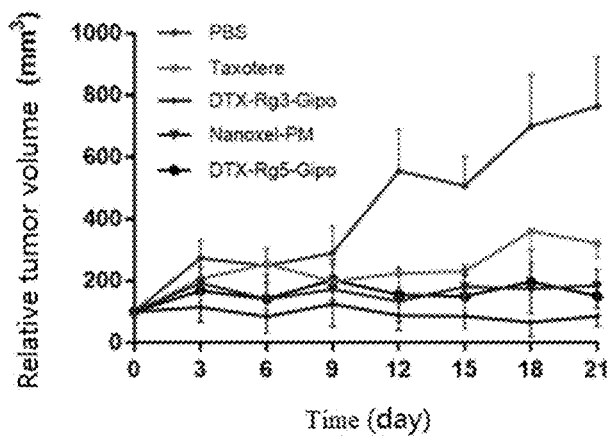
FIG. 11 is the relative tumor volume of Control group, Taxotere group, Nanoxel-PM group, DTX-Rg5-Gipo group and DTX-Rg3-Gipo group against human breast cancer cell line (4T1).

As shown in Table 9 and FIG. 11, after the same period of time, the volume of tumor in the PBS group is the maximum while in the DTX-Rg3-Gipo group is the minimum, followed by the DTX-Rg5-Gipo group and Nanoxel-PM group that are basically equivalent. The results suggest that DTX-Rg3-Gipo group has better anti-tumor activity.

Application Embodiment 8

In Vivo and In Vitra Pharmacological Efficacy Assay 8.1. In Vitro Drug Efficiency Assay A total of 10 different concentrations of each sample were set up as shown in Table 10. The survival rate of rat glioma C6 cells with addition of Rg3 group, Rg3-blank group, PTX group, PTX+Rg3 group, PTX-Cho-Lipo group and PTX-Rg3-Gipo group at various concentrations respectively are listed in Table 11 and FIG. 12.

TABLE 10

Concentrations of Rg3 group, Rg3-blank group, PTX group, PTX + Rg3 group, PTX-Cho-Lipo group and PTX-Rg3-Gipo group used to against rat glioma cells (C6)
C (μg/ml)

| Rg3 | Rg3-blank | PTX | PTX + Rg3 | PTX-Cho-Lipo | PTX-Rg3-Gipo |
|---|---|---|---|---|---|
| 20 | 20 | 10 | 10 | 10 | 10 |
| 6.67 | 6.67 | 3.333 | 3.333 | 3.333 | 3.333 |
| 2.22 | 2.22 | 1.111 | 1.111 | 1.111 | 1.111 |
| 0.74 | 0.74 | 0.370 | 0.370 | 0.370 | 0.370 |
| 0.25 | 0.25 | 0.1235 | 0.1235 | 0.1235 | 0.1235 |
| 0.08 | 0.08 | 0.0412 | 0.0412 | 0.0412 | 0.0412 |
| 0.03 | 0.03 | 0.0137 | 0.0137 | 0.0137 | 0.0137 |
| 0.01 | 0.01 | 0.0046 | 0.0046 | 0.0046 | 0.0046 |
| 0.003 | 0.003 | 0.0015 | 0.0015 | 0.0015 | 0.0015 |
| 0.001 | 0.001 | 0.0005 | 0.0005 | 0.0005 | 0.0005 |

TABLE 11

The viability of rat C6 glioma cells with addition of Rg3, Rg3-blank, PTX, PTX + Rg3, PTX-Cho-Lipo and PTX-Rg3-Gipo
Cell Viability

| Rg3 | Rg3-blank | PTX | PTX + Rg3 | PTX-Cho-Lipo | PTX-Rg3-Gipo |
|---|---|---|---|---|---|
| 89.02171 | 46.4009329 | 39.58829 | 31.71681 | 30.98532 | 22.91087 |
| 95.02171 | 65.10124 | 43.21006 | 33.91804 | 32.77745 | 23.9622 |
| 96.16015 | 78.86144 | 43.89464 | 34.35981 | 37.70992 | 24.9767 |
| 92.822 | 84.03477 | 45.97812 | 35.96694 | 38.48503 | 25.59589 |
| 95.42692 | 86.15499 | 49.90699 | 37.27702 | 45.13212 | 30.10103 |
| 94.23058 | 88.33881 | 60.48813 | 45.9984 | 50.08808 | 33.76731 |
| 92.03087 | 88.33881 | 65.36402 | 55.32691 | 59.15443 | 37.20547 |
| 92.41679 | 89.61094 | 73.2867 | 62.60873 | 72.80094 | 50.51328 |
| 98.82296 | 91.32832 | 79.49252 | 66.44756 | 85.5549 | 58.3184 |
| 100 | 100 | 100 | 100 | 100 | 100 |

Figure 12:
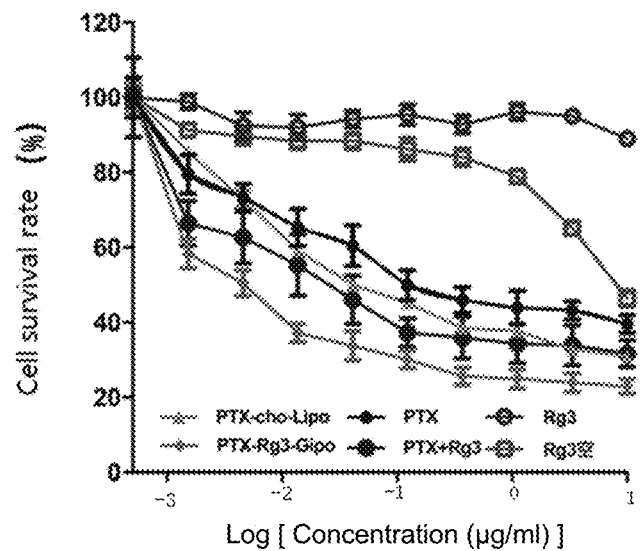
FIG. 12 is the cell survival rate of rat C6 glioma cells with addition of Rg3 Group, Rg3-Blank group, PTX Group, PTX+Rg3 group, PTX-Cho-Lipo group and PTX-Rg3-Gipo group.

As shown in Table 11 and FIG. 12, PTX-Rg3-Gipo group show better cell activity than PTX-Cho-Lipo group and PTX+Rg3 group. The results suggest that the cell activity of PTX-Rg3-Gipo group has been greatly improved.

8.2. Survival Curve and Median Survival Day

A total of 63 subcutaneous tumor-bearing nude mice were randomized into 7 groups (9 in each group), and intravenously injected with PBS solution (Control group,), Rg3, Rg3-blank, PTX, PTX+Rg3, PTX-Cho-Lipo and PTX-Rg3-Gipo via tail vein at a dose of 10 mg·kg$^{-1}$. From the 12$^{th}$ day after injection, the numbers of survived nude mice were recorded daily until all nude mice die. Survival curves of nude mice in each group were plotted by GraphPad Prism-5 software, and median survival time was calculated.

TABLE 12

The number of survived mice in each group at corresponding time against in-situ glioma

| Time(d) | PBS | PTX | Rg3 | PTX + Rg3 | PTX-Cho-Lipo | Rg3-blank | PTX-Rg3-Gipo |
|---|---|---|---|---|---|---|---|
| 12 | 9 | 10 | 10 | 10 | 10 | 10 | 10 |
| 14 | 9 | 10 | 10 | 10 | 10 | 10 | 10 |
| 16 | 8 | 9 | 9 | 9 | 10 | 10 | 10 |
| 18 | 6 | 8 | 9 | 9 | 10 | 10 | 10 |
| 20 | 5 | 7 | 8 | 7 | 9 | 9 | 10 |
| 22 | 4 | 6 | 7 | 6 | 8 | 9 | 10 |
| 24 | 3 | 6 | 7 | 6 | 8 | 9 | 9 |
| 26 | 3 | 5 | 6 | 5 | 7 | 9 | 9 |
| 28 | 2 | 4 | 5 | 3 | 6 | 7 | 8 |
| 30 | 0 | 4 | 4 | 3 | 5 | 5 | 8 |
| 32 | 0 | 4 | 4 | 3 | 5 | 5 | 8 |
| 34 | 0 | 3 | 3 | 1 | 4 | 4 | 7 |
| 36 | 0 | 1 | 3 | 1 | 3 | 3 | 7 |
| 38 | 0 | 1 | 2 | 0 | 3 | 3 | 7 |
| 40 | 0 | 0 | 1 | 0 | 3 | 2 | 7 |
| 42 | 0 | 0 | 0 | 0 | 3 | 2 | 7 |
| 44 | 0 | 0 | 0 | 0 | 3 | 2 | 6 |
| 46 | 0 | 0 | 0 | 0 | 3 | 2 | 6 |
| 48 | 0 | 0 | 0 | 0 | 2 | 2 | 6 |
| 50 | 0 | 0 | 0 | 0 | 2 | 2 | 5 |
| 52 | 0 | 0 | 0 | 0 | 2 | 1 | 5 |
| 54 | 0 | 0 | 0 | 0 | 1 | 1 | 5 |
| 56 | 0 | 0 | 0 | 0 | 1 | 1 | 5 |
| 58 | 0 | 0 | 0 | 0 | 0 | 1 | 3 |
| 60 | 0 | 0 | 0 | 0 | 0 | 0 | 1 |
| 62 | 0 | 0 | 0 | 0 | 0 | 0 | 0 |

TABLE 13

The median survival days in each group at corresponding time against in-situ glioma

| Groups | PBS | PTX | Rg3 | PTX + Rg3 | PTX-Cho-Lip | Rg3 | PTX-Rg3-Gipo |
|---|---|---|---|---|---|---|---|
| Median survival (day) | 21 | 27 | 29 | 27 | 35 | 32 | 54 |

Figure 13:
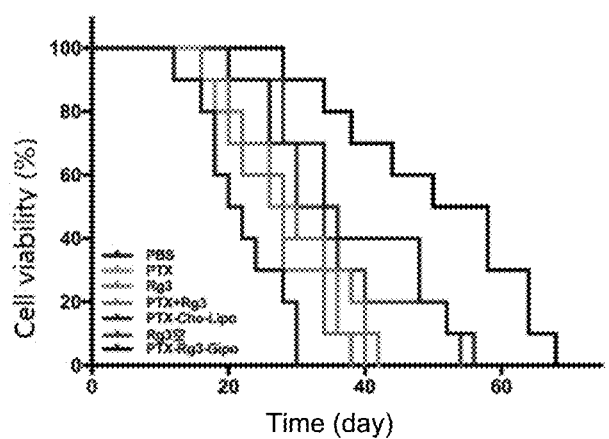
FIG. 13 is the cell survival rate of in-situ glioma model (C6 cells) with addition of Control Group, PTX group, Rg3 Group, Rg3-Blank group, PTX+Rg3 group, PTX-Cho-Lipo group and PTX-Rg3-Gipo group

As shown in Table 12, Table 13 and FIG. 13, the median survival time of PTX-Rg3-Gipo group is significantly longer than those of PTX-Cho-Lip group and PTX+Rg3 group.

Application Embodiment 9

In Vivo and In Vivo Pharmacological Efficacy Assay

1. In Vitro Cell Viability Assay

A total of 9 different concentrations were set up as shown in Table 12. The survival rate of human gastric cancer cells (BGC-823) with addition of Rg5 group, Rg3 group, Rh2 group, Rg5-blank group, Rg3-blank group, Rh2-blank group, PTX group, PTX-Cho-Lipo group, PTX-Rg5-Gipo group, PTX-Rg3-Gipo group and PTX-Rh2-Gipo group at various concentrations are shown in FIG. 12 and Table 14 respectively.

TABLE 14

Concentrations of Rg5 group, Rg3 group, Rh2 group, Rg5-blank group, Rg3-blank group, Rh2-blank group, PTX group, PTX-Cho-Lipo group, PTX-Rg5-Gipo group, PTX-Rg3-Gipo group and PTX-Rh2-Gipo group used in human gastric cancer cells (BGC-823)

| C(μg/mL) | | | | | | | | | | |
|---|---|---|---|---|---|---|---|---|---|---|
| Rg5 | Rg3 | Rh2 | Rg5-blank | Rg3-blank | Rh2-blank | PTX | PTX-Cho-Lipo | PTX-Rg5-Gipo | PTX-Rg3-Gipo | PTX-Rh2-Gipo |
| 0.0109 | 0.0109 | 0.0109 | 0.0109 | 0.0109 | 0.0109 | 0.0027 | 0.0027 | 0.0027 | 0.0027 | 0.0027 |
| 0.0329 | 0.0329 | 0.0329 | 0.0329 | 0.0329 | 0.0329 | 0.0082 | 0.0082 | 0.0082 | 0.0082 | 0.0082 |
| 0.0987 | 0.0987 | 0.0987 | 0.0987 | 0.0987 | 0.0987 | 0.0246 | 0.0246 | 0.0246 | 0.0246 | 0.0246 |
| 0.2962 | 0.2962 | 0.2962 | 0.2962 | 0.2962 | 0.2962 | 0.0740 | 0.0740 | 0.0740 | 0.0740 | 0.0740 |
| 0.8888 | 0.8888 | 0.8888 | 0.8888 | 0.8888 | 0.8888 | 0.2222 | 0.2222 | 0.2222 | 0.2222 | 0.2222 |
| 2.6666 | 2.6666 | 2.6666 | 2.6666 | 2.6666 | 2.6666 | 0.6666 | 0.6666 | 0.6666 | 0.6666 | 0.6666 |
| 8 | 8 | 8 | 8 | 8 | 8 | 2 | 2 | 2 | 2 | 2 |
| 24 | 24 | 24 | 24 | 24 | 24 | 6 | 6 | 6 | 6 | 6 |

TABLE 15

Cell viability of human gastric cancer cells (BGC-823) with addition of Rg5 group, Rg3 group, Rh2 group, Rg5-blank group, Rg3-blank group, Rh2-group, PTX group, PTX-Cho-Lipo group, PTX-Rg5-Gipo group, PTX-Rg3-Gipo group and PTX-Rh2-Gipo group Cell Viability

| Rg5blank | Rg3blank | Rh2blank | PTX | PTX-Cho-Lipo | PTX-Rg5-Gipo | PTX-Rg3-Gipo | PTX-Rh2-Gipo |
|---|---|---|---|---|---|---|---|
| 102.7 | 100.6 | 101.2 | 91.9 | 100.5 | 82.6 | 94.8 | 85.4 |
| 101.2 | 101.4 | 103.7 | 80.5 | 85.5 | 52.6 | 87.6 | 68.6 |
| 103.3 | 98.0 | 100.7 | 60.9 | 53.9 | 38.8 | 69.8 | 36.4 |
| 100.0 | 87.6 | 102.0 | 50.3 | 43.6 | 35.3 | 35.5 | 32.1 |
| 100.4 | 77.9 | 100.8 | 41.6 | 38.4 | 34.7 | 29.3 | 29.2 |
| 104.4 | 72.7 | 89.3 | 42.7 | 36.0 | 34.0 | 28.9 | 28.7 |
| 99.8 | 64.6 | 75.6 | 38.0 | 34.9 | 33.3 | 25.5 | 28.3 |
| 94.8 | 58.8 | 65.6 | 33.2 | 33.1 | 23.5 | 24.2 | 24.3 |
| 92.7 | 53.5 | 57.7 | 32.2 | 32.8 | 20.7 | 6.8 | 17.6 |

Figure 14:
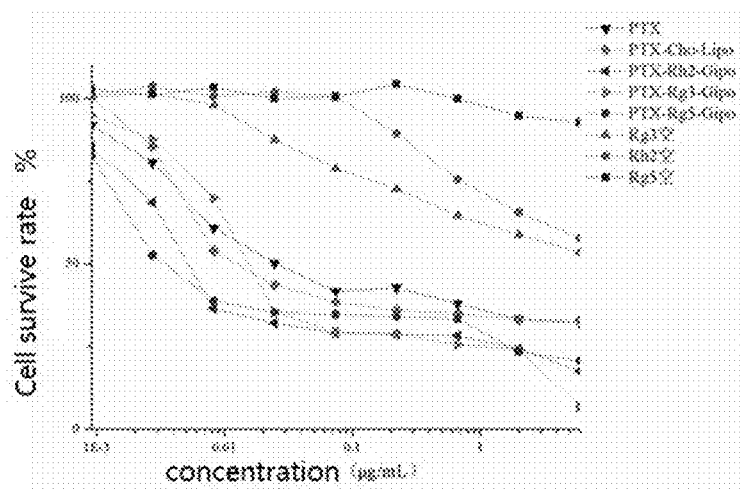

As shown in Table 15 and FIG. 14, the cell viability in PTX-Rg5-Gipo group, PTX-Rh2-Gipo group and PTX-Rg3-Gipo group are the best, followed by PTX-Cho-Lipo group and PTX group.

2. In vivo pharmacological efficacy assay: A total of 72 subcutaneous tumor-bearing nude mice were randomized into 8 groups (9 in each group), and intravenously injected with PBS solution (Control group,), Rg3, Rg3-blank, PTX-Cho-Lipo, Abraxane, PTX-Rg5-Gipo, PTX-Rg3-Gipo and PTX-Rh2-Gipo, via tail vein at a dose of 10 mg·kg$^{1}$. The changes of mice body weights in each group were recorded every 2 days, and the longest diameter and the shortest diameter of tumors were measured with vernier calipers. The tumor volume is calculated by the following formula: V=(dmax×dmin$^2$)/2, wherein dmin and dmax are respectively the shortest diameter and the longest diameter (mm) of the tumor; a relative tumor volume (RTV) is calculated according to the measurement results by the formula: RTV=TVn/TV$_0$, wherein TVn is the volume of the tumor measured every 2 days, TV$_0$ is the volume of the tumor measured at day zero (the administration day).

Figure 15:
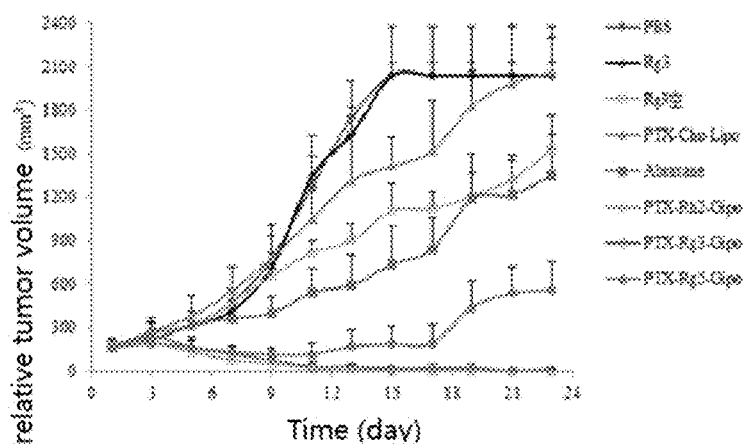
FIG. 15 is the relative tumor volume of control group, Rg3 Group, Rg3-Blank group, PTX-Cho-Lipo group, Abraxane group, PTX-Rg5-Gipo group, PTX-Rg3-Gipo group and PTX-Rh2-Gipo group against human gastric cancer cells (BGC-823).

Experimental results are listed in Table 16 and FIG. 15.

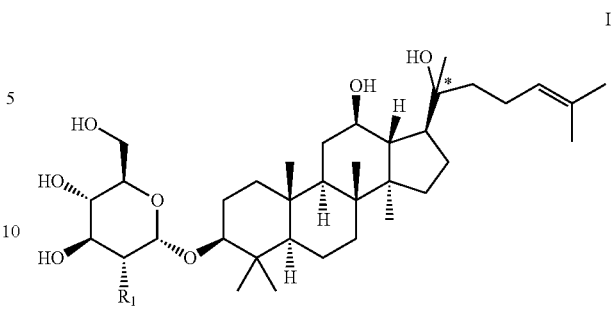

TABLE 16

Drug efficacy of Control group, Rg3 group, Rg3-blank group,
PTX-Cho-Lipo group,
Abraxane group, PTX-Rg5-Gipo group, PTX-Rg3-Gipo group and
PTX-Rh2-Gipo group
against human gastric cancer cell (BGC-823)
Relative tumor volume

| BGC-823 time(d) | PBS | Rg3 | Rg3-blank | PTX-Cho-Lipo | Abraxane | PTX-Rg5-Gipo | PTX-Rg3-Gipo | PTX-Rh2-Gipo |
|---|---|---|---|---|---|---|---|---|
| 1 | 164.67 | 166.88 | 168.24 | 165.27 | 164.67 | 165.77 | 163.63 | 163.50 |
| 3 | 215.94 | 267.38 | 275.58 | 275.58 | 225.78 | 187.97 | 239.71 | 197.10 |
| 5 | 322.94 | 317.96 | 319.38 | 381.27 | 316.77 | 165.73 | 161.94 | 134.83 |
| 7 | 469.00 | 417.96 | 472.85 | 553.90 | 362.70 | 134.84 | 119.29 | 79.99 |
| 9 | 777.24 | 717.96 | 657.85 | 782.11 | 401.47 | 115.01 | 78.56 | 53.36 |
| 11 | 1273.61 | 1340.69 | 817.79 | 1044.41 | 541.84 | 119.72 | 31.50 | 22.67 |
| 13 | 1747.54 | 1636.89 | 901.41 | 1313.14 | 595.41 | 171.04 | 30.04 | 23.87 |
| 15 | 2039.45 | 2034.43 | 1107.42 | 1410.32 | 736.65 | 186.47 | 15.40 | 6.83 |
| 17 | 2039.45 | 2034.43 | 1118.43 | 1515.96 | 840.69 | 193.32 | 18.89 | 4.05 |
| 19 | 2039.45 | 2034.43 | 1207.42 | 1826.55 | 1187.35 | 439.52 | 19.96 | 1.71 |
| 21 | 2039.45 | 2034.43 | 1321.36 | 1982.04 | 1215.19 | 535.77 | 4.14 | 2.00 |
| 23 | 2039.45 | 2034.43 | 1525.74 | 2061.15 | 1351.30 | 560.69 | 13.96 | 3.24 |

As shown in Table 16 and FIG. 15, after the same period of time, the tumor volume in Control group is the maximum while in the PTX-Rg3-Gipo group and the PTX-Rh2-Gipo group are the minimum, followed by the PTX-Rg5-Gipo group, the Abraxane group and PTX-Cho-Lipo group. The data suggest that PTX-Rg3-Gipo group and PTX-Rh2-Gipo group have significant better anti-tumor activity.

It is to be understood that the foregoing description of two preferred embodiments is intended to be purely illustrative of the principles of the invention, rather than exhaustive thereof, and that changes and variations will be apparent to those skilled in the art, and that the present invention is not intended to be limited other than expressly set forth in the following claims.

The invention claimed is:

1. A blank liposome having a membrane, wherein the membrane comprises a lipid and a ginsenoside of Formula I:

wherein,
"*" represents a chiral carbon;
R$^1$ is H, R$^{10}$, R$^{11}$ or hydroxy (OH);
R$^{10}$ is selected from the group consisting of: —O-Glc, —O-Rha, —O-Lyx, —O-Xyl, —O-Ara(p), —O-Ara(f), —O-Glc(2→1)Glc, —O-Glc(6→1)Glc, —O-Glc(2→1)Rha, —O-Glc(2→1)Xyl, —O-Glc(6→1)Xyl, —O-Glc(6→1)Rha, —O-Glc(2→1)Ara(p), —O-Glc(6→1)Ara(p), —O-Glc(2→1)Ara(f), —O-Glc(6→1)Ara(f), —O-Glc(2→1)Glc(2→1)Glc, —O-Glc(2→1)Glc(2→1)Xyl, —O-Glc(6→1)Glc(6→1)Xyl, —O-Glc(2→1)Glc(4→1)Xyl, —O-Glc(2→1)Lyx, —O-Glc(6→1)Lyx, —O-Glc(2→1)Glc(2→1)Rha, —O-Glc(2→1)Glc(2→1)Lyx, —O-Glc(2→1)Glc(2→1)Ara(f), —O-Glc(2→1)Glc(2→1)Ara(p), —O-Glc(2→1)Glc(6→1)Glc, —O-Glc(2→1)Glc(6→1)Rha, —O-Glc(2→1)Glc(6→1)Xyl, —O-Glc(2→1)Glc(6→1)Lyx, —O-Glc(2→1)Glc(6→1)Ara(f), —O-Glc(2→1)Glc(6→1)Ara(p), —O-Glc(6→1)Glc(2→1)Glc, —O-Glc(6→1)Glc(2→1)Rha, —O-Glc(6→1)Glc(2→1)Xyl, —O-Glc(6→1)Glc(2→1)Lyx, —O-Glc(6→1)Glc(2→1)Ara(f), —O-Glc(6→1)Glc(2→1)Ara(p), —O-Glc(6→1)Glc(6→1)Glc, —O-Glc(6→1)Glc(6→1)Rha, —O-Glc(6→1)Glc(6→1)Lyx, —O-Glc(6→1)Glc(6→1)Ara(f) and —O-Glc(6→1)Glc(6→1)Ara(p); wherein Glc is glucopyranosyl, Xyl is xylopyranosyl, Rha is Rhamnopyranosyl, Ara(p) is arabinopyranosyl, Ara(f) is arabinofuranosyl, Lyx is Lyxosyl; number indicates carbon position, arrow (4) indicates the connection relationship, and the same hereinafter;

$R^{11}$ is a group formed by replacing one or more OH groups in $R^{10}$ with $R^{10}$, and each of the one or more than one $R^{10}$ groups is independently the same as or different from each other.

2. The blank liposome of claim 1, wherein, $R^1$ is OH or

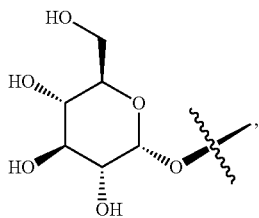

wherein the carbon marked with "*" is in S-configuration.

3. The blank liposome of claim 1, wherein the ginsenoside of Formula I is Ginsenoside Rg3 or Rh2.

4. The blank liposome of claim 1, wherein the lipid is a phospholipid and the phospholipid is natural phospholipid, semi-synthetic phospholipid, or fully synthetic phospholipid; the mass ratio of the phospholipid to the ginsenoside of Formula I is in a range of 0.5:1-100:1, or 2:1-20:1, or 3:1-10:1.

5. The blank liposome of claim 1, wherein the membrane further comprises cholesterol; the mass ratio of the cholesterol to the ginsenoside is in a range of 0.01:1-100:1, or 0.1:1-10:1, or 0.5:1-2:1.

6. The blank liposome of claim 1, wherein the membrane further comprises a long-circulating material; the mass ratio of the long-circulating material to the ginsenoside of Formula I is in a range of 0.01:1-10:1, or 0.1:1-5:1, or 0.1:1-1:1.

7. The blank liposome of claim 1, further comprising a cryoprotectant, wherein the mass percentage of the cryoprotectant to the total mass of the blank liposome is in a range of 0.5-70%, or 5-60%, or 30-60%.

8. The blank liposome of claim 1, further comprising an antioxidant, wherein the mass percentage of the antioxidant to the total mass of the blank liposome is in a range of 0.001-15%, or 0.01-10%, or 0.01-5%.

9. The blank liposome of claim 1, further comprising a soybean oil, a sodium oleate, or both, wherein the mass percentage of either or both of the soybean oil and sodium oleate to the total mass of the blank liposome is in a range of 1-30%, or 1-20%, or 1-10%; wherein the mass ratio of the soybean oil or sodium oleate to the lipid is in a range of 0.1:1-10:1, or 0.1:1-5:1.

10. The blank liposome of claim 1, further comprising a surfactant, a heat-sensitive excipient, a pH sensitive material, or an ionic additive.

11. The blank liposome of claim 4, wherein the phospholipid is egg lecithin, soybean lecithin, hydrogenated soy lecithin or Lipoid S100.

12. The blank liposome of claim 6, wherein the long-circulating material is selected from the group consisting of dimyristoyl phosphatidylethanolamine-PEG (DMPE-PEG), dipalmitoyl phosphatidylethanolamine-PEG (DPPE-PEG), distearoyl phosphatidylethanolamine-PEG (DSPE-PEG), dioleoyl phosphatidylethanolamine-PEG (DOPE-PEG), C8 PEG ceramide (C8 ceramide-PEG), C16 PEG ceramide (C16 ceramide-PEG), distearoyl phosphatidylethanolamine-PEG-succinyl (DSPE-PEG succinyl), distearoyl phosphatidylethanolamine-PEG-carboxyl (DSPE-PEG carboxylic acid), distearoyl phosphatidylethanolamine-PEG-maleimide (DSPE-PEG maleimide), distearoyl phosphatidylethanolamine-PEG-propionamide bis-mercaptopyridine (DSPE-PEG PDP), distearoyl phosphatidylethanolamine-PEG-cyanuric chloride (DSPE-PEG cyanur), distearoyl phosphatidylethanolamine-PEG-amino(DSPE-PEG amine), distearoyl phosphatidylethanolamine-PEG-biotin (DSPE-PEG biotin), distearoyl phosphatidylethanolamine-PEG-folate (DSPE-PEG folate), dilauroyl phosphatidylethanolamine-PEG (DLPE-PEG), distearoyl phosphatidylethanolamine-PEG-active succinimidyl ester (DSPE-PEG-NHS), phosphatidylethanolamine-PEG-active succinimidyl ester (DMPE-PEG-NHS), dipalmitoyl phosphatidylethanolamine-PEG-active succinimidyl ester (DPPE-PEG-NHS), dilauroyl phosphatidylethanolamine-PEG-active succinimidyl ester (DLPE-PEG-NHS), distearoyl phosphatidylethanolamine-PEG-maleimide(DSPE-PEG-maleimide), dimyristoyl phosphatidylethanolamine-PEG-maleimide (DMPE-PEG-maleimide), dipalmitoyl phosphatidylethanolamine-PEG-maleimide (DPPE-PEG-maleimide), dilauroyl phosphatidylethanolamine-PEG-maleimide (DLPE-PEG-maleimide), distearoyl phosphatidylethanolamine-PEG-biotin (DSPE-PEG-biotin), distearoyl phosphatidylethanolamine-PEG-fluorescein (DSPE-PEG-FITC), distearoyl phosphatidylethanolamine-PEG-hydroxyl (DSPE-PEG-OH), distearoyl phosphatidylethanolamine-PEG-amino(DSPE-PEG-NH2), phosphatidylethanolamine-PEG-amino (DMPE-PEG-NH2)dipalmitoyl phosphatidylethanolamine-PEG-amino (DPPE-PEG-NH2), dilauroyl phosphatidylethanolamine-PEG-amino (DLPE-PEG-NH2), distearoyl phosphatidylethanolamine-PEG-carboxyl (DSPE-PEG-COOH), dimyristoyl phosphatidylethanolamine-PEG-carboxyl (DMPE-PEG-COOH), dipalmitoyl phosphatidylethanolamine-PEG-carboxyl (DPPE-PEG-COOH), dilauroyl phosphatidylethanolamine-PEG-carboxyl (DLPE-PEG-COOH), distearoyl phosphatidylethanolamine-PEG-thiol (DSPE-PEG-SH), distearoyl phosphatidylethanolamine-PEG-silane (DSPE-PEG-silane), distearoyl phosphatidylethanolamine-PEG-azide (DSPE-PEG-N3), cholesterol-PEG (cholesterol PEG), methoxyl-PEG-cholesterol (mPEG-CLS), cholesterol-PEG-active succinimidyl ester (cholesterol PEG NHS ester), cholesterol-PEG-maleimide (CLS-PEG-Mal), cholesterol-PEG-biotin (cholesterol PEG biotin), cholesterol-PEG-fluorescein (cholesterol PEG fluorescein), cholesterol-PEG-carboxyl (cholesterol PEG COOH), cholesterol-PEG-amino (cholesterol-PEG-$N_H2$) and cholesterol-PEG-thiol Cholesterol-PEG-SH) preferably, and 1,2-distearoyl-sn-glycero-3-phosphoethanolamine (DSPE)-PEG2000.

13. The blank liposome of claim 7, wherein the cryoprotectant comprises a sugar, a polyol, an amino acid or a buffer reagent.

14. The blank liposome of claim 8, wherein the antioxidant is selected from the group consisting of sodium metabisulfite, sodium thiosulfate, propyl gallate, ascorbic acid, α-tocopherol, α-hydroxyl acid, flavonoid, phenylpropanoid, vitamin E, vitamin C, fumaric acid, cysteine, methionine, butylhydroxy anisole, butylated hydroxytoluene, thiodipropionic acid, sulfites, hydrosulphite, dithioaminobenzoic acid, citric acid, malic acid, sorbitol, glycerol, propylene glycol, hydroquinone, hydroxycoumarin, ethanolamine, phosphoric acid and phosphorous acid.

15. The blank liposome of claim 10, wherein the surfactant comprises polyethylene glycol or polysorbate.

16. The blank liposome of claim 10, wherein the heat-sensitive excipient comprises a heat-sensitive polymer and/ or a heat-sensitive surfactant; wherein the heat-sensitive polymer comprises polypropylene acrylamide, polypropylene acrylic acid, polyphoester, or poly(ester amide) copolymer; wherein the heat-sensitive surfactant comprises a Tween surfactant or Brij surfactant.

17. The blank liposome of claim 10, wherein the ionic additive comprises a cationic additive or an anionic additive.

18. The blank liposome of claim 17, wherein the cationic additive is octadecylamine; wherein the anionic additive is phosphatidic acid or phosphatidylserine.

19. A process for preparing the blank liposome of claim 1, comprising:
   step (1): mixing the lipid and the ginsenoside of Formula I together in an organic solvent to obtain a clear solution, optionally, with one or more agents selected from a cholesterol, a long-circulating material, a hydrophobic antioxidant, a soybean oil, a sodium oleate, a hydrophobic surfactant, a hydrophobic heat-sensitive excipient, a hydrophobic pH sensitive material and a hydrophobic ionic additive; wherein the organic solvent is one or more solvents selected from alcohols, halogenated hydrocarbon solvents, and nitrile solvents; wherein the ginsenoside of Formula I is micronized into ultrafine powder with an average particle size no more than 50 μm; or no more than 20 μm, or no more than 10 μm; and
   step (2): removing the organic solvent from the clear solution obtained from step (1) to form a film, mixing the film with an aqueous solution comprising a cryoprotectant, optionally, with one or more agents selected from a hydrophilic antioxidant, a hydrophilic surfactant, a hydrophilic heat-sensitive excipient, a hydrophilic pH sensitive material, and a hydrophilic ionic additive to give a mixture; performing an operation of sonication or high pressure homogenization, filtering the mixture to obtain an aqueous solution containing the blank liposome, drying the aqueous solution to obtain the blank liposome of claim 1;
   wherein the lipid and the ginsenoside of Formula I are the same as those in claim 1.

20. The process of claim 19, wherein in step (1), the halogenated hydrocarbon solvent is $C_{1-4}$ halogenated hydrocarbon solvent, $C_{1-2}$ halogenated hydrocarbon solvent, chloroform, dichloromethane or dichloroethane; wherein the alcohol is $C_{1-4}$ alcohol solvent, $C_{1-3}$ alcohol solvent, methanol, ethanol, n-propanol, isopropyl alcohol or n-butanol; wherein the nitrile solvent is acetonitrile.

21. An active substance-loaded liposome comprising a blank liposome of claim 1 and an active substance.

22. The active substance-loaded liposome of claim 21, wherein the active substance is an anti-cancer drug; wherein the mass ratio of the active substance to the ginsenoside of Formula I is in a range of 0.1:1-10:1, or 0.5:1-2:1.

23. The active substance-loaded liposome of claim 21, wherein the anticancer drug is one or more drugs selected from the group consisting of paclitaxel, docetaxel, cabazitaxel, tesetaxel, ortataxel, larotaxel, simotaxel, irinotecan hydrochloride, hydroxycamptothecin, aminocamptothecin, 7-ethyl-10-hydroxy camptothecin, cisplatin, carboplatin, oxaliplatin, harringtonine, homoharringtonine, triptolide, cytarabine, etoposide phosphate, desoxy-podophyllotoxin, huperzine-A, vinorelbine tartrate, vincristine sulfate, vinblastine sulfate, epothilone A, epothilone B, epothilone C, epothilone D, epothilone E, epothilone F, decitabine, arsenic trioxide ($As_2O_3$), all-trans retinoic acid, Azithromycin, daunorubicin, pingyangmycin, doxorubicin hydrochloride and idarubicin hydrochloride.

24. A process for preparing the active substance-loaded liposome of claim 21, comprising:
   step (1): mixing the lipid, the ginsenoside of Formula I and the active substance in an organic solvent to obtain a clear solution, optionally, with one or more agents selected from a cholesterol, a long-circulating material, a hydrophobic antioxidant, a soybean oil, sodium oleate, a hydrophobic surfactant, a hydrophobic heat-sensitive excipient, a hydrophobic pH sensitive material, and a hydrophobic ionic additive; wherein the solvent is one or more solvents selected from alcohols, halogenated hydrocarbon solvents and nitrile solvents; wherein the ginsenoside of Formula I is micronized into ultrafine powder and the average particle size is no more than 50 μm; or no more than 20 μm, or no more than 10 μm; and
   step (2): removing the organic solvent from the clear solution obtained in step (1) to form a film, mixing the film with an aqueous solution comprising a cryoprotectant, and optionally one or more agents selected from a hydrophilic antioxidant, a hydrophilic surfactant, a hydrophilic heat-sensitive excipient, a hydrophilic pH sensitive material, and a hydrophilic ionic additive to give a mixture; performing an operation of sonification or high pressure homogenization, filtering the mixture to obtain an aqueous solution containing the active substance-loaded liposome, drying the aqueous solution to obtain the active substance-loaded liposome of claim 21.

25. The process of claim 24, wherein in step (1), the organic solvent, the lipid and the ginsenoside of Formula I are the same as those in claim 19; wherein in step (2), the cryoprotectant is added after the aqueous solution of the active substance-loaded liposome is prepared.

26. The blank liposome of claim 13, wherein the cryoprotectant is selected from the group consisting of trehalose, glucose, sucrose, propylene glycol, glycerol, xylitol and ammonium sulfate.

27. The blank liposome of claim 14, wherein the antioxidant is selected from the group consisting of vitamin E, vitamin C, sodium thiosulfate and sodium sulfite.

28. The active substance-loaded liposome of claim 23, wherein the anticancer drug is paclitaxel, docetaxel, irinotecan, doxorubicin or cisplatin.

* * * * *